US008062222B2

(12) United States Patent
Dertinger et al.

(10) Patent No.: US 8,062,222 B2
(45) Date of Patent: Nov. 22, 2011

(54) METHOD FOR MEASURING IN VIVO HEMATOTOXICITY WITH AN EMPHASIS ON RADIATION EXPOSURE ASSESSMENT

(75) Inventors: Stephen D. Dertinger, Webster, NY (US); Jeffrey C. Bemis, Rochester, NY (US); Steven M. Bryce, Rochester, NY (US)

(73) Assignee: Litron Laboratories, Ltd., Rochester, NY (US)

( * ) Notice: Subject to any disclaimer, the term of this patent is extended or adjusted under 35 U.S.C. 154(b) by 339 days.

(21) Appl. No.: 12/139,166

(22) Filed: Jun. 13, 2008

(65) Prior Publication Data

US 2008/0311586 A1  Dec. 18, 2008

Related U.S. Application Data

(60) Provisional application No. 60/943,625, filed on Jun. 13, 2007.

(51) Int. Cl.
 *A61B 5/00* (2006.01)
 *C12Q 1/68* (2006.01)
(52) U.S. Cl. .............................. 600/368; 435/6
(58) Field of Classification Search .................. None
 See application file for complete search history.

(56) References Cited

U.S. PATENT DOCUMENTS

| 4,751,188 | A | * | 6/1988 | Valet ............................ 436/63 |
|---|---|---|---|---|
| 5,858,667 | A | | 1/1999 | Dertinger et al. |
| 6,100,038 | A | | 8/2000 | Dertinger et al. |
| 6,140,067 | A | | 10/2000 | Anderson et al. |
| 2003/0134305 | A1 | | 7/2003 | Dertinger et al. |
| 2003/0175831 | A1 | | 9/2003 | Canton et al. |
| 2005/0026197 | A1 | | 2/2005 | Dertinger |
| 2006/0040291 | A1 | | 2/2006 | Dertinger et al. |
| 2006/0088874 | A1 | | 4/2006 | Bacher et al. |
| 2007/0274919 | A1 | | 11/2007 | Dertinger |

OTHER PUBLICATIONS

Terstappen, WMM and Loken, MR. Five-Dimensional Flow Cytometry as a New Approach for Blood and Bone Marrow Differentials; Cytometry, vol. 9 (1988) pp. 548-556.*
Medical Management of Radiation Accidents—Manual on the Acute Radiation Syndrome; Edited by Fliedner, TM, Friesecke I and Beyrer K. Published by the British Insitute of Radiology (2001).*
Valet, G. A New Method for Fast Blood Cell Counting and Partial Differentiation by Flow Cytometry; Blut, vol. 49 (1984) pp. 83-90.*
Benderitter et al., "Clearance of Radiation-Induced Apoptotic Lymphocytes: Ex Vivo Studies and an In Vitro Co-Culture Model," Radiation Research 158:464-474 (2002).
Azizova et al., "Predictability of Acute Radiation Injury Severity," Health Physics 94(3):255-263 (2008).
Parker et al., "Estimating Radiation Dose from Time to Emesis and Lymphocyte Depletion," Health Physics 93(6):701-704 (2007).
Dieye et al., "Absolute CD4 T-Cell Counting in Resource-Poor Settings," Acquir. Immune Defic. Syndr. 39(1):32-37 (2005).
Sundararajan Jayaraman, "Flow Cytometric Determination of Mitochondrial Membrane Potential Changes During Apoptosis of T Lymphocytic and Pancreatic Beta Cell Lines: comparison of Tetramethylrhodamineethylester (TMRE), Chloromethyl-X-Rosamine (H2-CMX-Ros) and MitoTracker Red 580 (MTR580)," Journal of Immunological Methods 306:68-79 (2005).
Boreham et al., "Radiation-Induced Apoptosis in Human Lymphocytes: Potential as a Biological Dosimeter," Health Physics 71:685-691 (1996) (abstract onlu).
International Search Report for International Patent Application PCT/US08/66978 (Sep. 2, 2008).

* cited by examiner

*Primary Examiner* — Rebecca Prouty
*Assistant Examiner* — Paul Martin
(74) *Attorney, Agent, or Firm* — LeClairRyan, a Professional Corporation

(57) ABSTRACT

The present invention relates a method for assessing in vivo hematotoxicity. The method utilizes differential staining of nucleated and non-nucleated blood cells, and also differential labeling of cells with functional versus dysfunctional mitochondrial membrane potential. Quantitative analyses can be conducted on stained whole blood specimens, and is based on blood cells' fluorescent emission and light scatter properties following exposure to an excitatory light source. The ratio of certain cell populations can be readily measured. Furthermore, it is also possible to express cell population values in terms of number per unit volume. This invention can be used to evaluate the hematotoxicity of drugs, chemicals, radiation, and other exogenous agents, or the effects that a suspected protective agent may have on induced hematotoxicity. Furthermore, the matrix of measurements provided by this invention is useful in estimating radiation dose, i.e., retrospectively. Kits for practicing the invention are also disclosed.

17 Claims, 18 Drawing Sheets

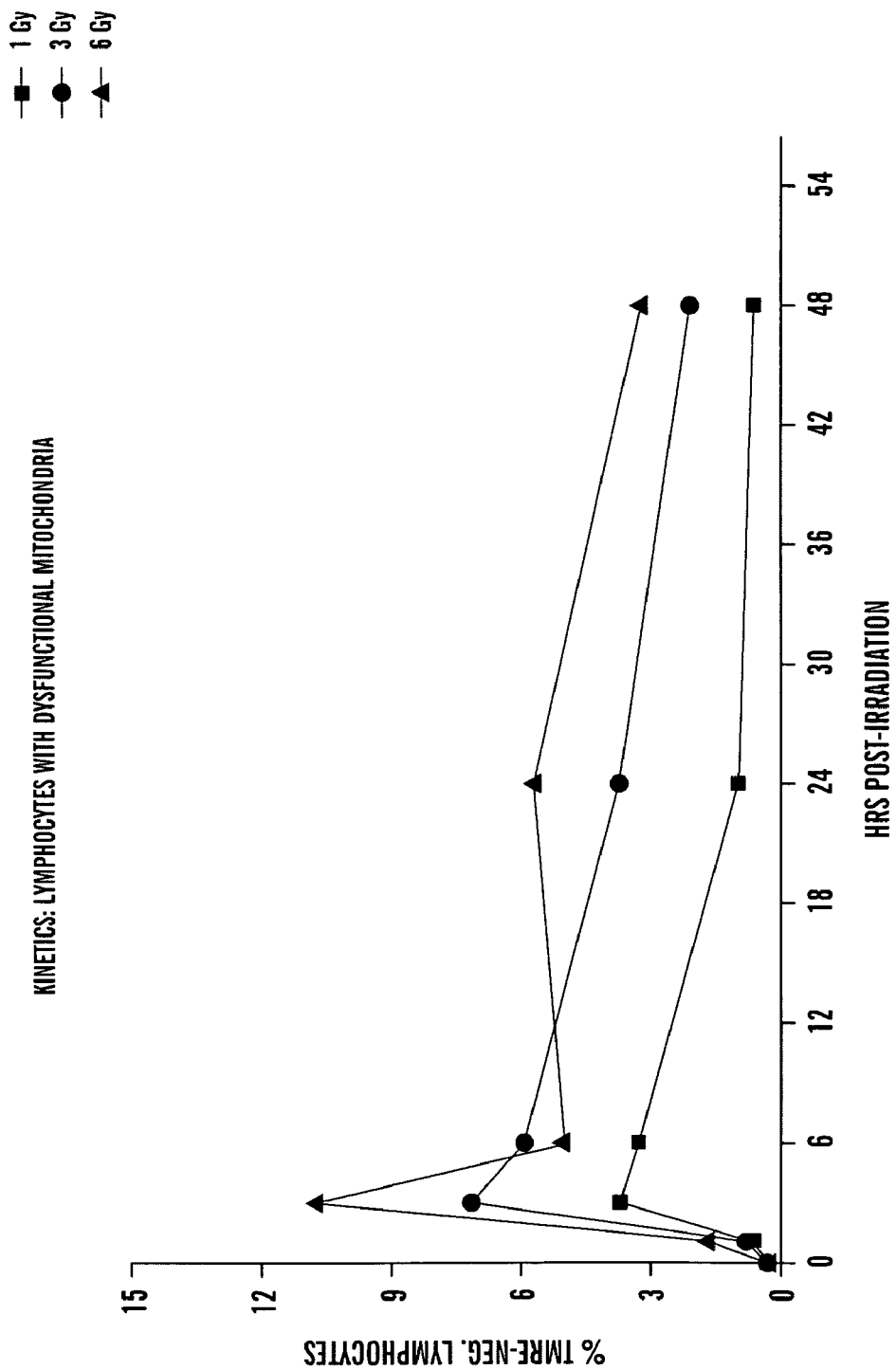

METHOD FOR MEASURING IN VIVO HEMATOTOXICITY WITH AN EMPHASIS ON RADIATION EXPOSURE ASSESSMENT

This application claims the priority benefit of U.S. Provisional Patent Application Ser. No. 60/943,625, filed Jun. 13, 2007, which is hereby incorporated by reference in its entirety.

FIELD OF THE INVENTION

This invention relates to an analytical method for measuring the frequency and also the absolute numbers of blood cells. The assay provides additional information regarding cell health as reflected by mitochondrial membrane potential, and is especially useful for assessing the extent of hematotoxicity associated with in vivo drug, chemical, or radiation exposure. Furthermore, the assay provides a matrix of measurements that are useful for radiation biodosimetry, that is, to estimate dose based on in vivo responses to radiation.

BACKGROUND OF THE INVENTION

Blood cells, including erythrocytes, lymphocytes, neutrophils, and monocytes, as well as non-cellular components such as platelets, serve specialized life-sustaining roles. It follows, then, that a method that can evaluate drugs, environmental factors, radiation exposures, or other agents for their ability to adversely affect stem cells, fully differentiated blood cells, or any intermediate stage cell, would be extremely useful for hazard identification purposes. This is one important application of the present invention.

Large-scale accidental, terrorist, or warfare-related radiation exposure scenarios will severely challenge the nation's medical community. The most effective allocation of resources will be required, especially in the hours and days immediately following a disaster, when many critical treatment decisions must be made. Thus, in order to deal with large-scale radiological events, there is a need for assays that supply information regarding dose distribution to tissue compartments of greatest clinical significance. The present invention addresses this need by representing a high throughput system that can be used to rapidly estimate radiation dose based on perturbations to the hematopoietic system. As described herein, these measurements can be accomplished with microliter quantities of blood, with minimal processing steps, and with currently available instrumentation.

One well known radiation biodosimetry assay is based on the kinetics by which lymphocytes are depleted from peripheral blood circulation following exposure to radiation (Goans et al., Health Phys. 81, 446-449 (2001)).

The kinetics of depletion is considered more useful than a single measurement, since the latter does not provide a very specific indicator of radiation exposure due to the amount of inter-individual variation that exists in the human population.

Depletion of lymphocytes from circulation, as well as many other significant manifestations of toxicity, can often be attributed to programmed cell death, or apoptosis. An early event in the apoptotic program is loss of mitochondrial membrane potential. Some fluorescent dyes accumulate in mitochondria in proportion to their membrane potential. Thus, decreased or altered fluorescent intensity denotes mitochondrial dysfunction, and these staining characteristics have been widely used to detect cells undergoing apoptosis. Relevant to the invention disclosed herein, it has been observed that among several apoptosis labeling techniques, assessing loss of mitochondrial membrane potential is particularly advantageous in regard to detecting blood lymphocytes that have been damaged by ionizing radiation (Benderitter et al., Radiation Res., 158, 464-474 (2002)). These authors speculate that elimination of dying lymphocytes by phagocytes limits the value of other methods that detect apoptotic cells based on features that occur downstream of mitochondrial perturbations. Even so, the blood processing techniques employed by these investigators is less than ideal for radiation biodosimetry purposes in at least two respects. Firstly, Benderitter et al isolated blood lymphocytes on a Ficoll-Histopaque gradient, and subsequently washed the cells two times before accomplishing quantitative analysis. These extra processing steps require time, labor, reagents, and equipment that the invention described herein does not. Secondly, these processing steps have the potential to introduce errors in terms of cell enumeration, as well as assessments of cell health.

It would be desirable, therefore, to provide an analysis of markers that enhance the value of both single and dual time-point lymphocyte counts for the purpose of radiation dose estimation. The present invention is directed to overcoming this deficiency of the prior art.

SUMMARY OF THE INVENTION

A first aspect of the present invention relates to a method for enumeration of blood cells and blood platelets to assess the degree of hematotoxicity resulting from exposure to a hazardous exogenous agent. This method includes the steps of: providing a blood sample from a mammal exposed to a hazardous exogenous agent, the blood sample comprising erythrocytes, reticulocytes, nucleated cells, and platelets; first contacting a portion of the sample of known volume with a nucleic acid dye that has a fluorescent emission spectrum and differentially labels mature erythrocytes, reticulocytes, and leukocytes based on their nucleic acid content; second contacting the portion of the sample with a second fluorescent reagent that is responsive to mitochondrial membrane potential and thereby differentially labels healthy and damaged cells, the second fluorescent reagent having a fluorescent emission spectrum that does not substantially overlap with the fluorescent emission spectrum of the nucleic acid dye; exciting the nucleic acid dye and second fluorescent reagent with light of appropriate excitation wavelength; and detecting the fluorescent emission and light scatter produced by erythrocytes, reticulocytes, platelets and nucleated cells in the portion of the sample, and counting for the portion of the sample two or more endpoints selected from the group of (i) the frequency of reticulocytes, (ii) the frequency of reticulocytes with dysfunctional mitochondria, (iii) the frequency of reticulated platelets, (iv) the frequency of platelets with dysfunctional mitochondria, (v) the frequency of reticulated platelets with dysfunctional mitochondria, (vi) the frequency of lymphocytes with dysfunctional mitochondria, (vii) the frequency of neutrophils with dysfunctional mitochondria, (viii) the absolute number of lymphocytes, (ix) the absolute number of platelets, and (x) the absolute number of neutrophils, wherein the counting of two or more endpoints assesses the degree of hematotoxicity resulting from exposure to the hazardous exogenous agent.

In a preferred embodiment of the first aspect of the invention, a portion of a blood specimen (of known volume) is contacted with each of the fluorescent reagents simultaneously. In certain cases, it can be advantageous to analyze each specimen two times: firstly, using a forward light scatter threshold, and secondly, using a fluorescence threshold that is set sufficiently high so as to exclude ("gate out") platelets and erythrocytes based on their relatively low nucleic acid dye associated fluorescence signals. In this manner, it is possible to focus analyses on erythrocyte populations and platelets during the first round of data acquisition, and nucleated cells in a second, without the need for separate samples or the use of erythrocyte lysis procedures.

The following measurements are then available once sufficient numbers of particles have been evaluated: (i) the frequency of reticulocytes, (ii) the frequency of reticulocytes with dysfunctional mitochondria, (iii) the frequency of reticulated platelets, (iv) the frequency of platelets with dysfunctional mitochondria, (v) the frequency of reticulated platelets with dysfunctional mitochondria, (vi) the frequency of lymphocytes with dysfunctional mitochondria, and (vii) the frequency of neutrophils with dysfunctional mitochondria. Furthermore, using one or more approaches, it is possible to express certain populations, for instance lymphocytes, platelets, and neutrophils, in terms of cell number per unit volume. Changes to one or more of these parameters following exposure to the exogenous agent under consideration reflect manifestations of toxicity. Any two or more of these parameters, up to and including all ten of the parameters, can be relied upon for assessing the degree of toxicity.

A second aspect of the present invention relates to a method of assessing radiation exposure of an individual. This method includes the steps of: performing the method according to the first aspect of the present invention on a single blood sample; identifying the amount of time elapsed between the exposure event and the providing of the single blood sample; and comparing the results obtained from the single blood sample, with expected values for unexposed mammals, for two or more of the endpoints, wherein deviation from the expected values, in consideration of the elapsed time, indicates the dose level of radiation exposure.

A third aspect of the present invention relates to a method of assessing radiation exposure. This method includes the steps of: performing the method according to the first aspect of the present invention on two or more blood samples obtained from the mammal, the two or more blood samples being obtained at different time points relative to the radiation exposure; identifying the amount of time elapsed between the radiation exposure event and the providing of the two or more blood samples; and comparing the results obtained from the two or more blood samples for two or more of the endpoints, wherein the rate at which endpoint values change, the magnitude of endpoint value change, or the combination thereof, indicates the level of radiation exposure.

A fourth aspect of the present invention relates to a method of evaluating the effects of an exogenous agent that can modify hematotoxicity. This method includes the steps of: administering to a mammal an exogenous agent that may modify hematotoxicity, and a known hematotoxic agent; performing the method according to the first aspect of the present invention on a blood sample obtained from the mammal to obtain two or more endpoints; and comparing the two or more endpoint values for the mammal with endpoint values obtained for unexposed mammals and/or mammals exposed to the known hematotoxic agent, wherein a significant deviation in two or more endpoints indicates the degree to which the exogenous agent can modify hematotoxicity.

A fifth aspect of the present invention relates to a kit that includes: a nucleic acid dye that has a fluorescent emission spectrum and differentially labels mature erythrocytes, reticulocytes, and nucleated cells based on their nucleic acid content; a second fluorescent reagent that is responsive to mitochondrial membrane potential and thereby differentially labels healthy and damaged cells, the second fluorescent reagent having a fluorescent emission spectrum that does not substantially overlap with the fluorescent emission spectrum of the nucleic acid dye; one or more balanced salt solutions; and optionally a solution comprising fluorescent microspheres present at a known concentration, the fluorescent microspheres having a fluorescent emission spectrum that does not substantially overlap with the fluorescent emission spectra of the nucleic acid dye or the second fluorescent reagent.

The present invention identifies procedures that can be employed for an automated assay that can be used to evaluate agents (i.e., chemical or physical) for in vivo hematotoxicity. It can also be used to detect occupational, accidental, other unintentional toxicant exposure scenarios. Furthermore, this assay is useful for estimating radiation dose.

BRIEF DESCRIPTION OF THE DRAWINGS

FIG. 1A demonstrates that some cell permeant nucleic acid dyes, in conjunction with light scatter properties, can resolve platelets, erythrocytes (RBCs), and nucleated cells. FIG. 1B shows that when regions and gates are appropriately configured, it is possible to focus analyses on erythrocyte populations, and further to determine the percentage of immature erythrocytes (reticulocytes) as a percentage of all erythrocytes.

FIG. 2A demonstrates that healthy reticulocytes, especially young reticulocytes, stain with nucleic acid dyes due to their RNA content, and TMRE-positive due to the presence of mitochondria. FIG. 2B shows that when regions and gates are appropriately configured, it is possible to focus analyses on reticulocytes, and further to determine the percentage of TMRE-negative reticulocytes. FIG. 2C shows that when data acquisition is triggered on a sufficiently high FL1 fluorescence channel, and when light scatter is collected in linear scale, it is possible to exclude platelets and erythrocytes from analysis. This allows one to enumerate particular nucleated cell populations, for example lymphocytes in this example. FIG. 2D shows that it is possible to focus on particular nucleated cell populations, for instance lymphocytes in this example, and to determine the percentage of TMRE-negative lymphocytes.

FIG. 3A=lymphocytes; FIG. 3B=platelets; and FIG. 3C=reticulocytes. As shown here, dose related responses were observed for the lymphocyte count, percentage of lymphocytes with dysfunctional mitochondria, percentage of reticulocytes, and percentage of reticulocytes with dysfunctional mitochondria. Conversely, at these doses and at this one time point, no significant effect was observed for the platelet count or the percentage of reticulated platelets.

FIG. 4A demonstrates that when data acquisition is triggered on a sufficiently high FL1 fluorescence channel, and when light scatter is collected in linear scale, it is possible to exclude platelets and erythrocytes from analysis. This allows one to enumerate microspheres ("beads") as well as particular nucleated cell populations, for example lymphocytes in this example. FIG. 4B shows that it is possible to focus on particular nucleated cell populations, for instance lymphocytes in this example, and to determine the percentage of TMRE-negative lymphocytes as a percentage of all lymphocytes. As this specimen was from a healthy volunteer, the percentage of TMRE-negative lymphocytes is very low. FIG. 4C illustrates the low TMRE-associated fluorescence of lymphocytes that have lost their mitochondrial membrane potential (in this case, through ex vivo treatment with carbonyl cyanide 3-chlorophenylhydrazone).

FIG. 5A=lymphocytes; and FIG. 5B=reticulocytes. As shown here, the percentage of lymphocytes is decreased by 1 Gy irradiation, with no appreciable protection afforded by amifostine. Reticulocytes are also found to decrease given 1 Gy treatment, with a marked increase in the percentage of reticulocytes with dysfunctional mitochondria. Unlike lymphocytes, reticulocyte effects are ameliorated by amifostine.

FIGS. 6A-B are graphs showing the effects that in vivo exposure to gamma rays has on two lymphocyte-associated endpoints measured in this invention. These time course data are from groups of female C57BL/6J mice exposed to 1, 3 or else 6 Gy. FIG. 6A=number of lymphocytes; and FIG. 6B=percentage of lymphocytes with dysfunctional mitochondria (i.e., % TMRE-negative). As shown here, the number of lymphocytes is decreased in a dose and time-dependent manner, whereas the frequency of TMRE-negative lymphocytes increases.

FIG. 7A=percentage of reticulocytes; and FIG. 7B=percentage of reticulocytes with dysfunctional mitochondria (i.e., % TMRE-negative). As shown here, the number of reticulocytes is decreased in a dose and time-dependent manner, whereas the frequency of TMRE-negative reticulocytes increases.

FIG. 8A=lymphocytes; and FIG. 8B=reticulocytes. As shown here, dose related responses were observed for the lymphocyte count, percentage of lymphocytes with dysfunctional mitochondria, percentage of reticulocytes, and percentage of reticulocytes with dysfunctional mitochondria.

DETAILED DESCRIPTION OF THE INVENTION

Figure 1B:
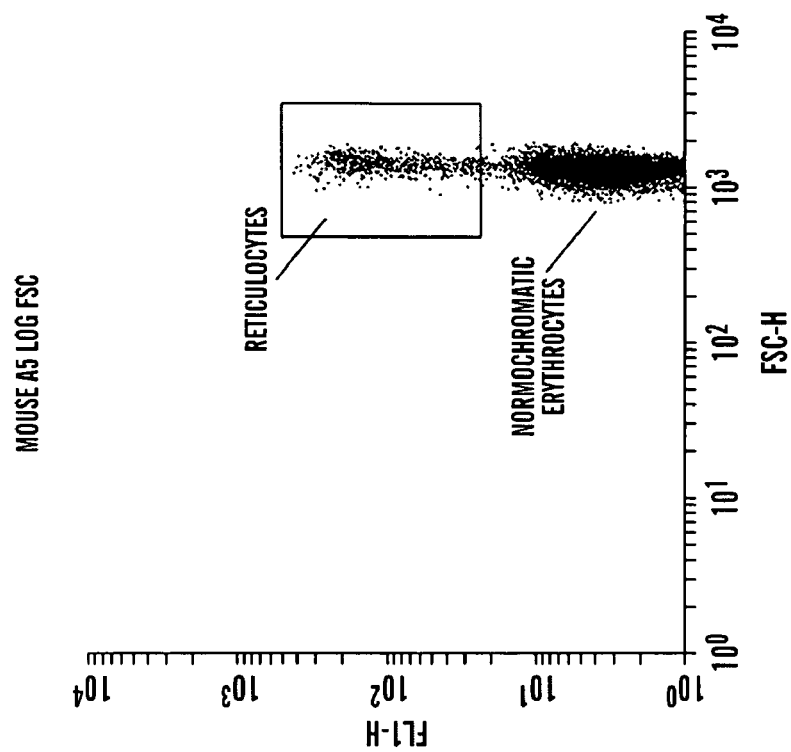
FIGS. 1A-B show bivariate plots resulting from flow cytometric analyses of a mouse blood specimen. In this example, whole blood was stained with thiazole orange (FL1 channel dye) and a known number of microspheres were included as counting beads.

The present invention is directed to a method for measuring the frequency and also the number of certain blood cell populations per unit volume using an optical device designed for illumination and analysis of cell specimens.

For purposes of the present invention, erythrocytes is intended to mean enucleated red blood cells, regardless of RNA content. For the purposes of the present invention, reticulocytes is intended to mean recently formed enucleated red blood cells, characterized by the presence of cytoplasmic RNA. For the purposes of the present invention, reticulated platelets is intended to mean recently formed platelets, characterized by the presence of RNA. For the purposes of the present invention, nucleated cells or leukocytes is intended to mean neutrophils, lymphocytes, monocytes, as well as all other less abundant nucleated cells that exist in peripheral blood circulation. For the purposes of the present invention, dysfunctional mitochondria is intended to mean cells which exhibit low mitochondrial membrane potential, that is, those that are presumably dead or dying (i.e., in various stages of apoptosis).

The advantageous characteristics of this invention relative to other in vivo hematotoxicity assays is that the staining procedures are very simple (effective staining does not require centrifugation), frequency and absolute cell counts can be acquired, and the matrix of measurements obtained provide a comprehensive assessment of cellular damage to multiple cell types. Other advantages will become apparent in the discussion of the various embodiments.

With this method, blood specimens are preferably obtained from mammals within hours or days after exposure. If blood samples happen to have been stored prior to exposure or if baseline measurements happen to have been made for an individual prior to exposure, then these baseline measurements can be used to compare any measurements obtained for a first time period following exposure. In addition, serial blood specimens can be collected over a period of time for a better understanding of the kinetics by which cell population(s) change.

In the simplest case, whole blood is stained according to procedures described herein. Alternately, whole blood may be added to an isotonic buffer and centrifuged at a speed that is sufficient to pellet cells. In this case it is important to note the original volume of blood that provided these "washed blood cells" so that absolute cell counts will still be possible. Thus, as used herein, the term "blood sample" can mean either whole blood or washed blood cells. Preferably, known volumes or portions of blood samples are used in the procedures of the present invention, which permits accurate cell counts per volume of blood.

The majority of flow cytometry applications that involve blood specimens focus on either red blood cells or leukocytes (but not both), and these applications typically call for their separation prior to analysis. That is because light scatter characteristics and most fluorescent reagents are not capable of distinguishing between these cell types, and because the presence of these other cell types often interfere with the quantitative analyses that are desired. Several techniques are commonly employed to physically separate blood cell types prior to flow cytometric analysis, and include: specialized centrifugation techniques, for instance with Ficoll-Histopaque; various immunochemical techniques, for instance through the use of cell-type specific immunoglobulins that have been coupled to paramagnetic beads; and osmotic challenges and/or detergents that are used to preferentially lyse erythrocytes. Such separation procedures require processing steps that require additional labor, reagents, and/or instrumentation. Furthermore, these steps may compromise the integrity of cells of interest. For these reasons, these steps or processes are preferably avoided in carrying out the present invention. Instead, the treatment of whole blood or washed blood cells in accordance with the present invention is much gentler on cells compared to standard practices of physical separation, and is ideal for an assay that intends to provide information regarding the health, or lack thereof, of cells as they existed in vivo.

To achieve hematotoxicity measurements according to the present invention, whole blood or washed blood cells are incubated with a reagent that crosses the membrane of cells and fluorescently labels nucleic acids. Preferably, the reagent differentially labels mature erythrocytes, reticulocytes, and nucleated cells.

Exemplary nucleic acid dyes include, without limitation, thiazole orange, SYTO® Green dyes #11-25 (inclusive), SYTO® Orange dyes #80-85 (inclusive), SYTO® Red dyes #17 and #59-64 (inclusive), SYTO® RNA Select™, and acridine orange. The choice of dye will depend on the excitation source, as well as the choice of other fluorochromes, so that a different fluorescence detector can be assigned to each fluorescent reagent. Preferred dyes include SYTO® Green dye 13, and thiazole orange.

Subsequent to or concurrent with differential labeling of mature erythrocytes, reticulocytes, and nucleated cells with the nucleic acid dye, a second reagent is added to the blood sample, one that labels cells undergoing apoptosis. Ideally, the reagent labels an early event in the programmed cell death cascade, thereby allowing for detection in blood before the reticuloendothelial system eliminates these compromised cells. A preferred reagent of this type will differentially label mitochondrial membranes depending on the membrane potential.

Exemplary mitochondrial membrane potential probes include, without limitation: tetramethylrhodamine methyl ester (TMRM); tetramethylrhodamine ethyl ester (TMRE); 3,3' dihexyloxacarbocyanine iodide ($DiOC_6$); 5,5',6,6'-tetrachloro-1,1',3,3'-tetraethylbenzimidazolcarbocyanine iodide (JC-1); 3,3-dimethyl-α-naphthoxacarbocyanine iodide (JC-9); 1,1',3,3,3',3'-hexamethylindodicarbocyanine iodide ($DilC_1$); nonylacridine orange; safranine O; and rhodamine-123. A preferred mitochondrial probe is TMRE.

As noted above, loss of mitochondrial membrane potential can be measured in blood lymphocytes that have been damaged by ionizing radiation (Benderitter et al, *Radiation Res.* 158:464-474 (2002), which is hereby incorporated by reference in its entirety). Besides blood lymphocytes, platelets and reticulocytes are other readily available blood constituents that house mitochondria. Thus, platelets and/or reticulocytes can also be used to study agents or conditions that can cause mitochondrial dysfunction. Labeling blood components with a mitochondrial membrane potential probe, especially leukocytes (for instance lymphocytes and/or neutrophils), and also reticulocytes, is an important aspect of the present invention.

While most flow cytometry applications involve quantifying the proportion of various cell populations, more recently practitioners of the art have been using these instruments to measure cells per unit volume ("absolute cell counts"). Several newer flow cytometers (e.g., CyFlo® ML and CyFlow® SL models from Partec North America, Inc., Mt. Laurel, N.J.) offer true volumetric absolute counting and therefore are able to accurately determine the amount of sample analyzed. This can then be used to calculate the total count of cells per volume. For example, knowing the volume of blood that was stained and the dilution factor associated with the staining process, as well as the sample volume analyzed, an accurate total cell count for lymphocytes, neutrophils, reticulocytes, and platelets can be calculated per unit volume of blood.

As an alternative, particularly when employing flow cytometry equipment that does not allow for determining accurately the volume of sample analyzed, a known number of microspheres can be added to the sample prior to scoring. As the number of these beads, the volume of blood that was stained, and the dilution factor associated with the staining process are known, it is possible to express flow cytometry-based cell counts on a per blood volume basis based on the numbers of beads analyzed per unit of sample.

When employed, these microspheres, sometimes called "counting beads," are added to the specimens. For instance, U.S. Pat. No. 5,627,037 to Ward et al., which is hereby incorporated by reference in its entirety, discloses a one-step method for determining absolute numbers of one or more populations of reticulocytes and/or leukocytes in a whole blood sample using flow cytometry. The method includes mixing a blood sample with a diluent containing a fixative, one or more fluorescent cell markers and a known number of fluorescent microspheres per unit volume. The prepared samples are analyzed by flow cytometry. The number of cells and the number of microparticles provide a ratio that can be used, knowing the number of microspheres per unit volume and the total sample volume, to calculate the absolute number of cells in the whole blood sample. A similar approach for determining absolute counts can be utilized by the invention disclosed herein.

Exemplary microspheres include, without limitation, beads that have a sedimentation rate that is approximately equal to cells, and that are of a size and/or fluorescence intensity that permits them to be differentiated from blood cells and platelets by a flow cytometer or similar device. Beads in the size range 1 to 10 microns are commonly used for this purpose, or else those that are used more generally to ensure that flow cytometers are in working properly (calibration beads).

As noted above, the fluorochromes and nucleic acid dye should be selected such that they can all be excited by the one or more light sources, yet their emission spectra are sufficiently distinct. Preferably, the emission maxima of the nucleic acid dye, mitochondrial membrane probe, and microspheres (if employed) do not substantially overlap (i.e., they have distinct emission maxima). With regard to their excitation spectra, it is preferable for these reagents to have similar excitation spectra because that affords the use of a single-laser flow cytometer.

Preferably, blood specimens are brought into contact with the various fluorescent reagents simultaneously, and incubated for a duration and at a temperature that is compatible with all cell types and fluorescent reagents. Exemplary durations and temperatures for staining are approximately 15 to 30 minutes at approximately 20 to 37° C. Thereafter, samples should be stored in the dark at room temperature, on ice, or at temperatures that are close to 4° C. (e.g., between 2° C. to about 8° C.). Of course, the buffer that is used to prepare the fluorescent reagents and that the blood specimens are added to also needs to be compatible with all cell types and fluorescent reagents. Exemplary isotonic buffers are phosphate-buffered saline (PBS) or Hank's Balanced Salt Solution (HBSS). These buffers may contain serum, for instance 1 to 10% (v/v) fetal bovine serum, to help maintain cell morphology and/or function.

Samples that have been contacted with the various fluorescent reagents as described should be protected from light until they are ready for analysis. In a preferred embodiment of the present invention, samples are analyzed on the same day as harvesting/staining.

Regardless of whether the samples are stored or treated the same day as harvested/stained, the treated sample can be subjected to optical detection and enumeration of blood cell subpopulations using any suitable optical detection system. Preferred optical detection systems have one or more light sources, preferably in the form of one or more amplified or collimated beams of light, that are able to excite the various fluorescent reagents. Exemplary optical detection systems include, without limitation, single-laser flow cytometers and dual- or multiple-laser flow cytometers.

Single-laser flow cytometric analysis uses a single focused laser beam with an appropriate emission band to excite all of the fluorescent reagents. As stained cells pass through the focused laser beam, they exhibit a fluorescent emission maxima characteristic of the fluorochromes or dyes associated therewith. The flow cytometer is equipped with appropriate detection devices to enable detection of the fluorescent emissions and light scatter produced by the cells. In this way, the following frequencies can be determined: reticulocytes among total erythrocytes; reticulocytes with dysfunctional mitochondria among reticulocytes; reticulated platelets among total platelets; reticulated platelets with dysfunctional mitochondria among total reticulated platelets; platelets with dysfunctional mitochondria among total platelets; lymphocytes with dysfunctional mitochondria among total lymphocytes; and neutrophils with dysfunctional mitochondria among total neutrophils. Furthermore, using the equipment or supplemental reagents noted above, it is possible to express certain populations as total cell counts per unit volume, for instance lymphocytes, neutrophils, reticulocytes, and platelets.

Dual- or multiple-laser flow cytometric analysis use two or more focused laser beams with appropriate emission bands, in much the same manner as described above for the single-laser flow cytometer. Different emission bands afforded by the two or more lasers allow for additional combinations of fluorescent dyes or immunochemical-conjugated fluorochromes to be employed.

According to a preferred approach for analyzing the sample(s), the samples are analyzed twice using an alternate thresholding technique. In a first step, the samples are analyzed using the nucleic acid dye fluorescence in combination with a low forward light scatter threshold. In a second step, the samples are analyzed using the nucleic acid dye fluorescence in combination with a high fluorescence threshold. This technique allows one alternately to focus on erythrocyte and platelet populations, and then on leukocytes.

In general, the present invention is intended to be practiced as follows: a known volume of blood (e.g., 10 μl from a finger-prick or else from a venipuncture specimen) is combined with the fluorescent reagents noted above (nucleic acid dye, mitochondrial membrane-potential sensitive dye, and optionally the fluorescent microspheres). After a sufficient amount of staining/labeling time has elapsed, specimens are ready for flow cytometric analysis. These fluorescent reagents, in conjunction with cells' light scatter properties, provide several measurements that are sensitive to hematotoxicity, for instance hematotoxicity resulting from radiation exposure, treatment with an anti-neoplastic drug, etc. A panel of measurements that reflect hematotoxicity can be acquired with this assay, and include absolute counts (expressed as per unit volume) as well as frequency measurements as noted above.

Any two or more of the above-described endpoints can be measured together to assess hematotoxicity. Alternatively, any three or more, any four or more, any five or more, any six or more, any seven or more, any eight or more, any nine or more, or all ten of the endpoints can be considered in an assessment of hematotoxicity. According to one embodiment, a cell population count of lymphocytes and one or more other cell type (e.g., neutrophils, platelets, and reticulated platelets) is used in combination with any two or more of reticulocytes with dysfunctional mitochondria among total reticulocytes, lymphocytes with dysfunctional mitochondria among total lymphocytes, neutrophils with dysfunctional mitochondria among total neutrophils, reticulated platelets among total platelets, and reticulocytes among total erythrocytes.

One application of the present invention relates to assessing the hematotoxicity of a drug, chemical, radiation, and other exogenous agents. In this case, an exogenous test agent is applied at one or several dose levels to a mammalian species. This test agent exposure may occur one or several times as is the case in acute or subacute toxicity tests, or repeatedly as is the case in subchronic and chronic toxicity tests. The test agent can be a chemical or formulation, or it can be a physical entity, such as ionizing radiation.

In this case, one or more blood specimens are obtained from mammals post-treatment. Pre-treatment blood specimens or else those collected from concurrent negative control group(s) can serve as a basis for comparison. These blood specimens are harvested and prepared for flow cytometric analysis according to procedures outlined above.

Certain agents may offer protection from hematotoxicity. The present invention can also be used to evaluate the efficacy of such agents. To assess the suspected protective effects of an agent, mammals can be exposed to the putative protective agent either prior to, concurrently, or soon after exposure to a toxic challenge. Any protective effect afforded by the agent can be measured relative to damage caused by the toxic challenge alone.

Owing to ionizing radiation's hematotoxicity, and the reproducibility of some of these responses, the present invention can also be used to estimate radiation dose. For this application, post-exposure data can be compared to expected values. Statistical approaches for converting cell count data into dose predictions are known. For instance, dose estimates from serial lymphocyte counts can be made using a lymphocyte depletion kinetic model based on previous responses in radiation accidents (Goans et al., *Health Phys.* 72:513-518 (1997), which is hereby incorporated by reference in its entirety). Similar methods can be applied to any one of the endpoints measured by this invention so long as the corresponding calibration curves have been developed. That being said, it may be preferable to combine two endpoints measured by the invention in a statistical model, and to estimate dose from this multi-parametric approach. One such applicable statistical model is likelihood theory. This general principle can be used to combine additional endpoints measured by this invention to better estimate the dose of irradiation using data acquired from a single sample. Alternately, if two or more specimens are available, the kinetics and/or magnitude by which the blood cell populations change can be used to estimate dose.

In regard to radiation biodosimetry, six endpoints are particularly advantageous, and are outlined in Table I below.

TABLE I

Matrix of In Vivo Hematotoxicity Endpoints with an Emphasis on Radiation Biodosimetry

| Population | Absolute Count | Frequency Measurement | Response to Radiation | Time Needed for Expression |
|---|---|---|---|---|
| Lymphocytes | Yes | | Decrease | hrs-days |
| Platelets | Yes | | Decrease | days-weeks |
| Reticulated Platelets | | Yes, relative to total platelets | Decrease | days-weeks |
| Reticulocytes | | Yes, relative to total erythrocytes | Decrease | days |
| Lymphocytes with dysfunctional mitochondria | | Yes, relative to total lymphocytes | Increase | hrs-days |
| Reticulocytes with dysfunctional mitochondria | | Yes, relative to total reticulocytes | Increase | hrs-days |

There are several characteristics of the invention that make it well suited for radiation biodosimetry purposes, including the low cost of reagents, fast data acquisition rate, and very simple blood handling steps. Furthermore, by tracking the frequency of lymphocytes and/or reticulocytes that express dysfunctional mitochondria, components of the matrix provide radiation dose information in less than one day, as opposed to other endpoints that either require greater lengths of time to express themselves, or that are less specific for radiation until serial blood samples become available.

There are at least two manners by which the invention may be implemented to provide dose estimates in the aftermath of a radionuclide disaster. One would be a so-called "reach back" scenario, whereby blood specimens are transported to off-site analysis facilities. In a second scenario, mobile labs would arrive at triage sites, hospitals, or other locations where exposed patients as well as the "worried well" are situated. These mobile labs would have the necessary flow cytometers and also kit-formatted fluorescent reagents that are required to execute these measurements. In either case, in conjunction with knowledge about blood collection time, flow cytometry data for single blood specimens would be compared to reference values as described briefly above. These single-point analyses would provide preliminary dose estimates. These samples can be used to categorize patients into a least two groups: significantly exposed or not. Subsequently, as serial samples become available, the kinetics by which the matrix of endpoints changes would provide more precise dose estimates.

EXAMPLES

The examples below are intended to exemplify the practice of the present invention but are by no means intended to limit the scope thereof.

Example 1

Cell Permeable Nucleic Acid Dye Plus Threshold Technique Allows Analyses to Focus Alternately on Erythrocytes and Platelets and then Nucleated Cells In this example, thiazole orange is used to differentially stain blood erythrocytes, reticulocytes, and nucleated cells. Fluorescent microspheres are used as counting beads. A fluorescence thresholding technique is described that enables analyses to focus on nucleated cells or alternately on erythrocytes and platelets.

Five mouse blood specimens (8-9 week old C57BL/6J) were collected from the tail vein of untreated female mice, and also from five age-matched mice that had been irradiated with 0.5 Gy gamma rays ($^{137}$Cs source) approximately 43 hours previously. These blood specimens were collected into a very low volume of heparin (10 µl of 500 units/ml), a volume that did not appreciably dilute the samples.

Figure 1A:
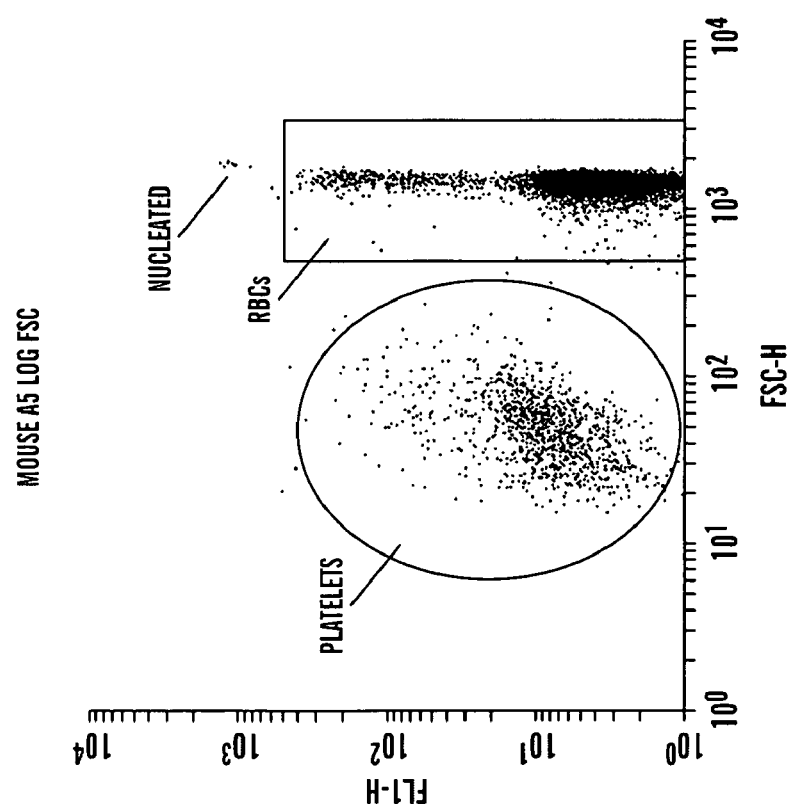
Figure 1D:
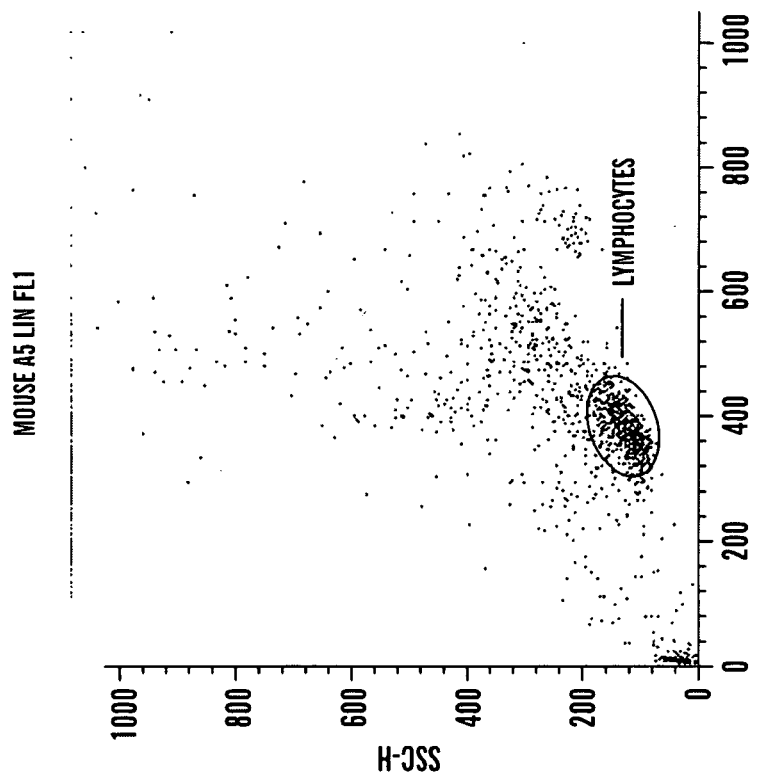
FIG. 1D shows that when data acquisition is triggered on a high nucleic acid dye-associated fluorescence signal, and when light scatter is collected in linear scale, it is possible to exclude platelets and erythrocytes from analysis, and to quantify particular nucleated cell populations, for instance lymphocytes in this example.
Figure 1C:
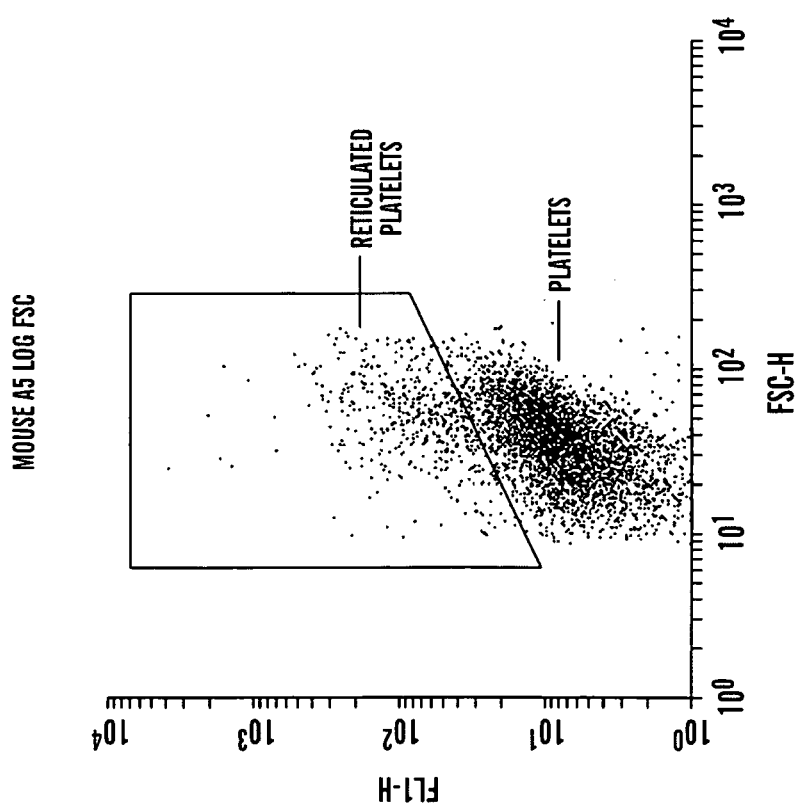
FIG. 1C shows that when regions and gates are appropriately configured, it is possible to focus analyses on platelets, and further to determine the percentage of newly formed platelets (reticulated platelets) as a percentage of all platelets.

To accomplish staining, 10 µl of whole blood were added to tubes containing thiazole orange at 0.08 ng/ml. This staining solution contained 20,720 counting beads per ml (beads from Molecular Probes, cat. no. C36950). After 45 minutes at room temperature, the samples were analyzed with a FACSCalibur flow cytometer providing 488 nm excitation. In the first round of analysis, a forward scatter threshold was used to trigger data acquisition. With the trigger channel set sufficiently low, platelets as well as all blood cell types were acquired. Thiazole orange associated fluorescence was collected with the FL1 detector, and as shown by FIG. 1A, this procedure was capable of resolving mature erythrocytes, reticulocytes, nucleated cells, platelets, and reticulated platelets, based on their light scatter characteristics and/or their different thiazole orange fluorescence intensities. As nucleated cells exhibit intense thiazole orange-associated fluorescence, these cells can be excluded from measurements that were directed at platelet and erythrocyte populations. Reticulocytes can thus be quantified as a percentage of all erythrocytes, and reticulated platelets can be quantified as a percentage of all platelets (FIGS. 1B-C). Data are provided in Table II below.

TABLE II

Reticulocyte and Platelet Values, C57BL/6J Mice

| Treatment | Avg. % Reticulocyte ± S.E.M. | Avg. % Reticulated Platelets ± S.E.M. | Avg. No. Platelets/L ± S.E.M. |
|---|---|---|---|
| Untreated | 4.16 ± 0.30 | 8.04 ± 1.10 | 6.44 × 10$^{11}$ ± 6.30 × 10$^{10}$ |
| Radiation | 3.02 ± 0.12 | 7.96 ± 0.35 | 8.24 × 10$^{11}$ ± 1.10 × 10$^{11}$ |

A second analysis was conducted with each of the ten stained blood specimens. Whereas acquisition had been triggered on forward light scatter and light scatter was acquired in log scale with the first analysis, the second analysis occurred with a FL1 threshold and light scatter was acquired in linear scale. Regarding the FL1 threshold, this was set sufficiently high so as to exclude platelets, mature erythrocytes and reticulocytes, thereby restricting acquisition to nucleated cells. By expressing light scatter in linear scale, it was possible to focus on particular subpopulations, for instance lymphocytes that are low in forward and side scatter relative to other nucleated cells (FIG. 1D). Since the counting beads are highly fluorescent, they were not excluded by the FL1 threshold, and their known density facilitated lymphocyte counting that can be expressed on a per volume basis (data are provided in Table III below).

TABLE III

Lymphocyte Values

| Treatment | No. Lymphocytes per L (± S.E.M.) |
|---|---|
| Untreated | $5.74 \times 10^9 \pm 4.19 \times 10^8$ |
| Radiation | $3.51 \times 10^9 \pm 1.96 \times 10^8$ |

This example demonstrates the ability of the invention to focus analyses on platelets and erythrocytes, and alternately on nucleated cells. This is accomplished by using a nucleic acid dye that resolves nucleated cells from other cell types as well as platelets based on their high nucleic acid content, coupled with thresholding that alternately is based on the forward light scatter and the FL1 parameter.

Example 2

Matrix of Radiation Sensitive Endpoints Using Mouse Blood

Building on the nucleic acid dye and thresholding technique described in the previous example, this example demonstrates the use of an additional fluorescent reagent that reports on mitochondrial membrane potential. Furthermore, this example demonstrates the sensitivity of several endpoints to ionizing radiation. For this experiment, SYTO®13 was used to differentially stain blood erythrocytes, reticulocytes, and nucleated cells. TMRE was used to as a mitochondrial membrane probe, and fluorescent latex beads were used as counting beads.

Mouse blood specimens (8-9 week old C3H/HeJ) were collected via heart puncture from female mice that were exposed to 0, 0.5, 1.0, 2.0 or 3.0 Gy gamma rays ($^{137}$Cs source; 3 mice per group). These blood specimens were collected approximately 44 hours post-exposure into a low volume of heparin that did not appreciably dilute the samples.

10 μl of whole blood were then added to tubes containing 2 ml PBS with SYTO®13 at 0.05 nM, TMRE at 100 nM, and 20,720 counting beads per ml (beads from Molecular Probes, cat. no. C36950). After 15 minutes at 37° C., the samples were moved to room temperature and analyzed with a FACSCalibur flow cytometer providing 488 nm excitation.

Figure 2B:
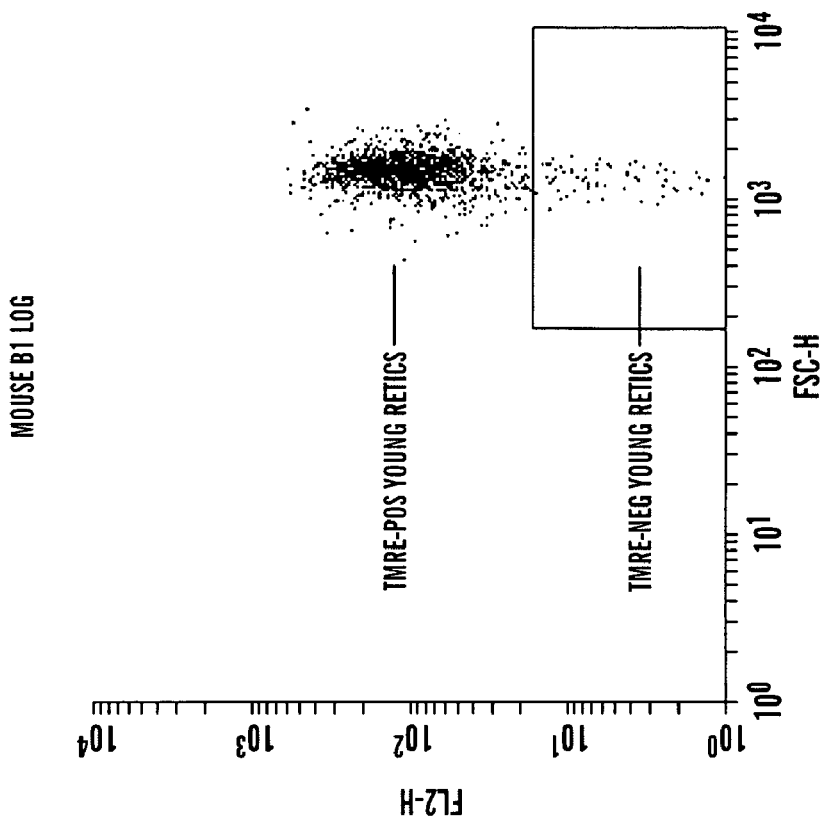
FIGS. 2A-D show bivariate plots from flow cytometric analyses of a mouse blood specimen. In this example, whole blood was simultaneously contacted with SYTO®13 (an FL1 channel cyanine dye available from Invitrogen Corp., Carlsbad, Calif.) and tetramethylrhodamine ethyl ester (TMRE; a FL2 channel dye). A known number of microspheres were included as counting beads.
Figure 2A:
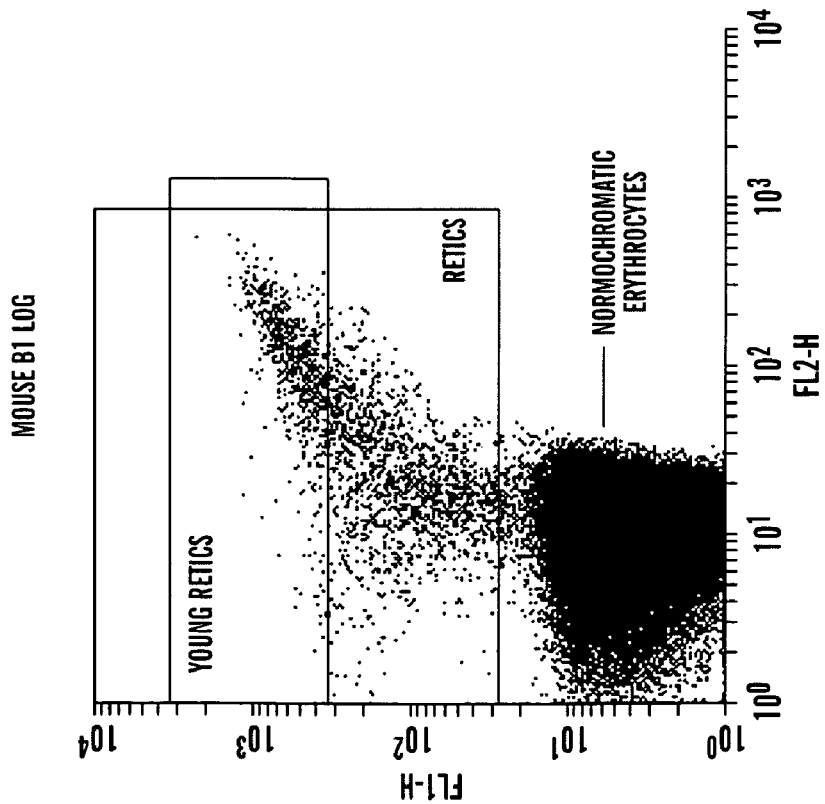

In the first round of analysis, a forward scatter threshold was used to trigger data acquisition. With the trigger channel set sufficiently low, platelets as well as all blood cell types were acquired. Similar to thiazole orange, SYTO®13 dye in conjunction with light scatter signals was capable of resolving mature erythrocytes, reticulocytes, nucleated cells, platelets, and reticulated platelets. As nucleated cells exhibit intense SYTO®13-associated fluorescence, these events can be excluded from measurements that were directed at platelet and erythrocyte populations. Reticulocytes can thus be quantified as a percentage of all erythrocytes, and reticulated platelets can be quantified as a percentage of all platelets. Furthermore, with the incorporation of the TMRE dye, it was possible to enumerate the percentage of reticulocytes that express dysfunctional mitochondrial membranes (FIGS. 2A-B).

Figures 2C, 2D:
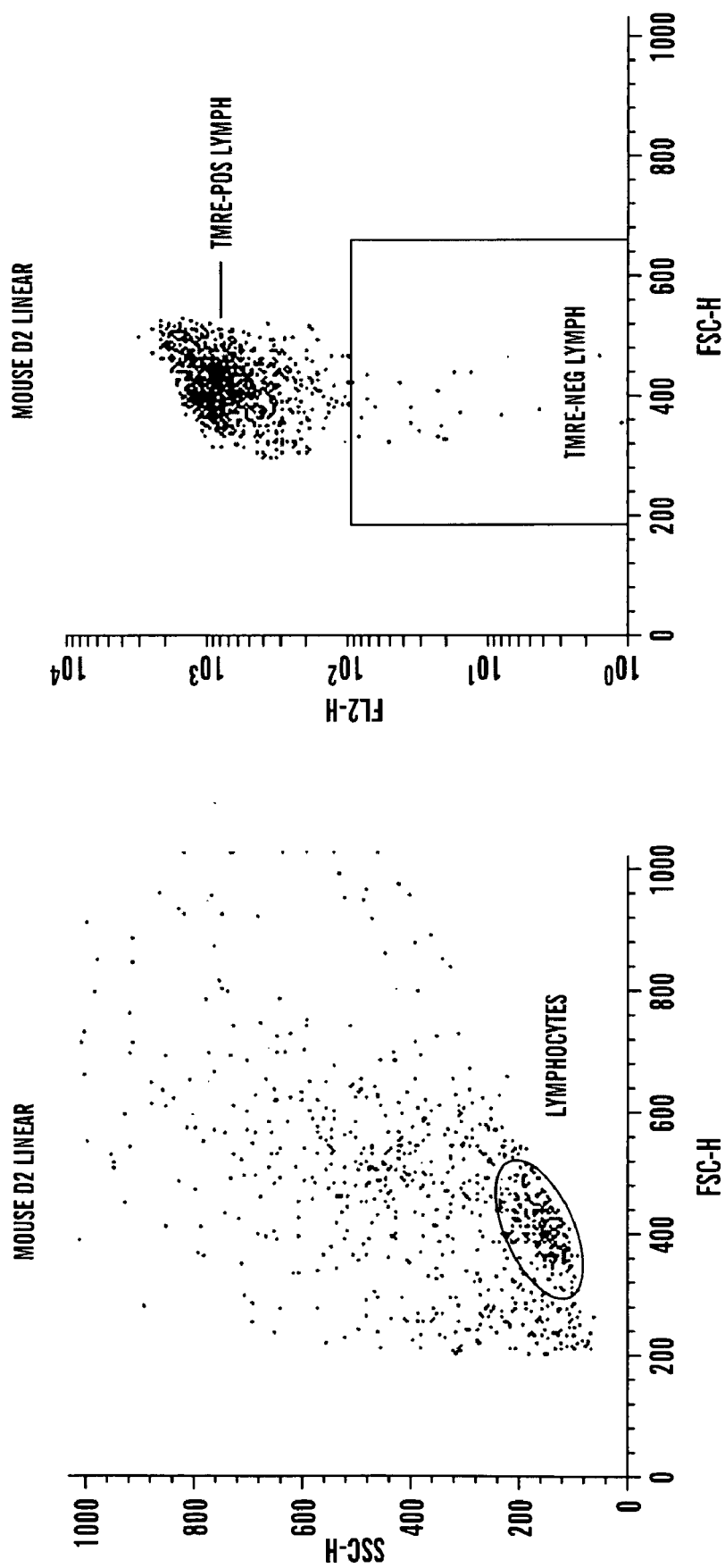

A second analysis was conducted with the stained mouse blood specimens. Whereas acquisition had been triggered on forward light scatter and light scatter was acquired in log scale with the first analysis, the second analysis occurred with a FL1 threshold and light scatter was acquired in linear scale. Regarding the FL1 threshold, this was set sufficiently high so as to exclude platelets, mature erythrocytes and reticulocytes, thereby restricting acquisition to nucleated cells. By expressing light scatter in linear scale, it was possible to focus on particular subpopulations, for instance lymphocytes that are low in forward and side scatter relative to other nucleated cells. Since the counting beads are highly fluorescent, they were not excluded by this FL1 threshold, and their known density facilitated lymphocyte counting that can be expressed on a per volume basis. Furthermore, with the incorporation of the TMRE dye, it was possible to enumerate the percentage of lymphocytes that express dysfunctional mitochondrial membranes (FIGS. 2C-D).

Figure 3A:
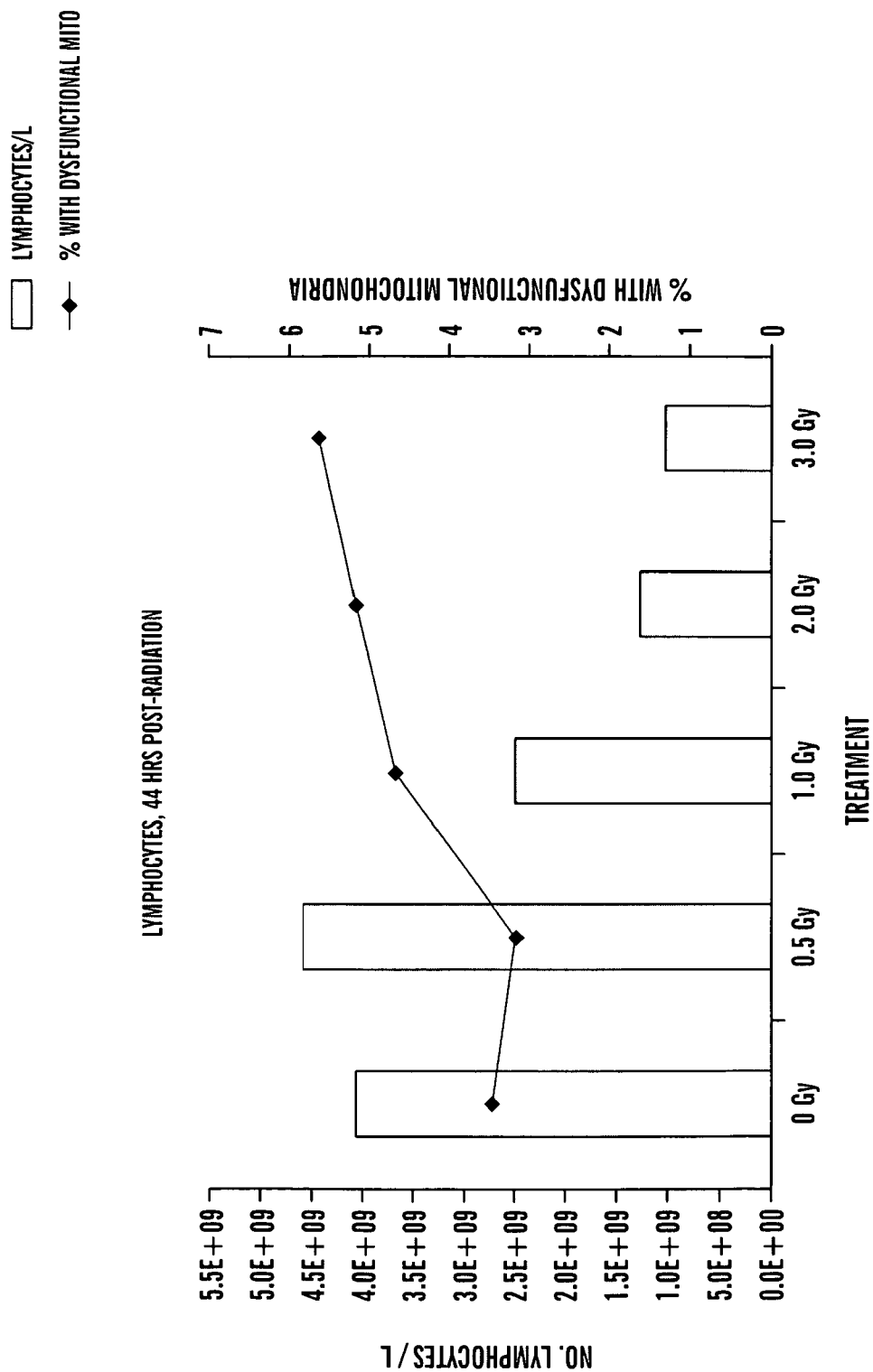
FIGS. 3A-C are graphs showing the effects that in vivo exposure to gamma rays has on six endpoints measured in this invention. These data are from groups of three C3H/HeJ mice exposed to 0, 0.5, 1, 2 or 3 Gy, with blood collected 44 hrs post-exposure.
Figure 3B:
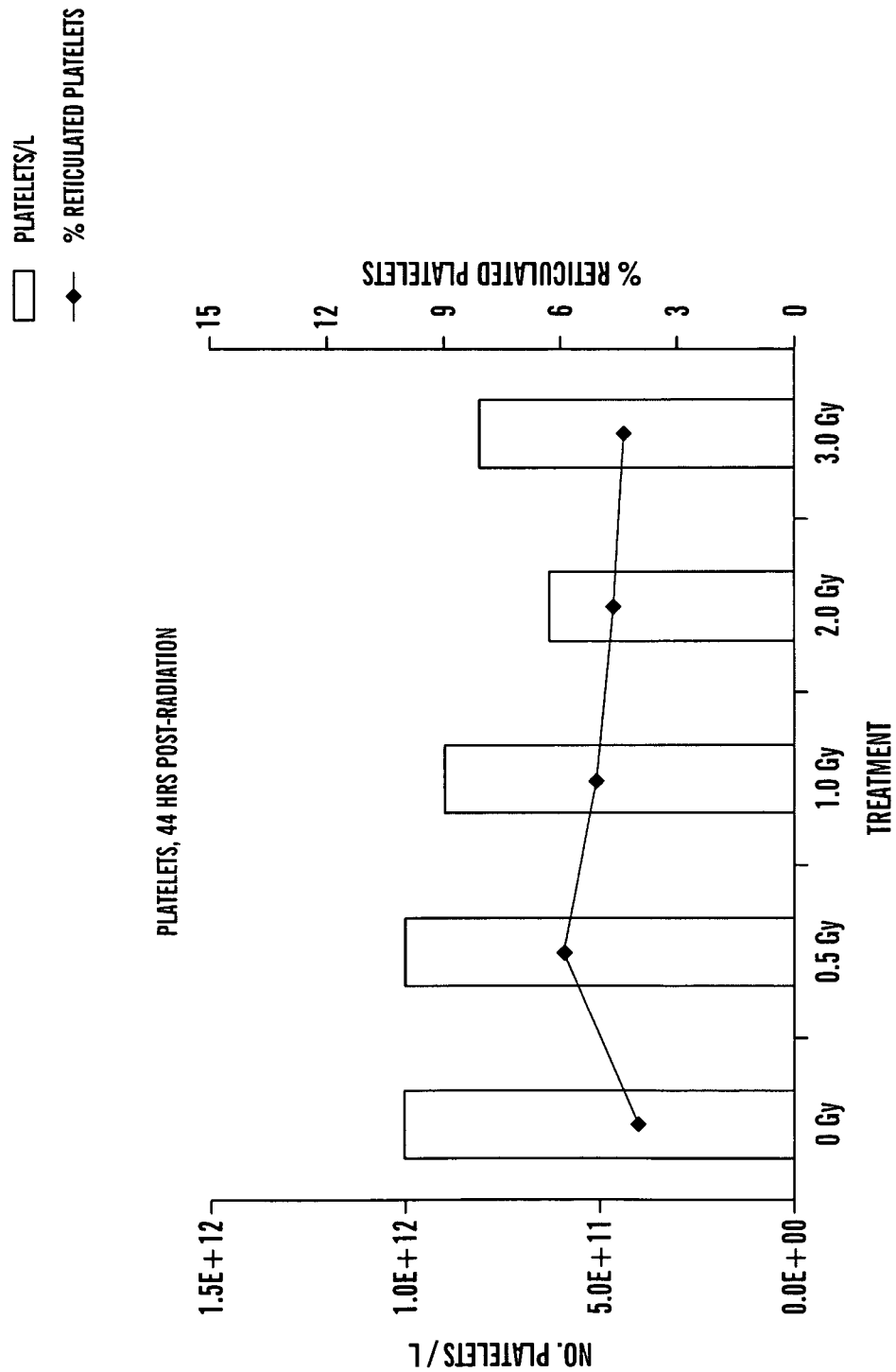
Figure 3C:
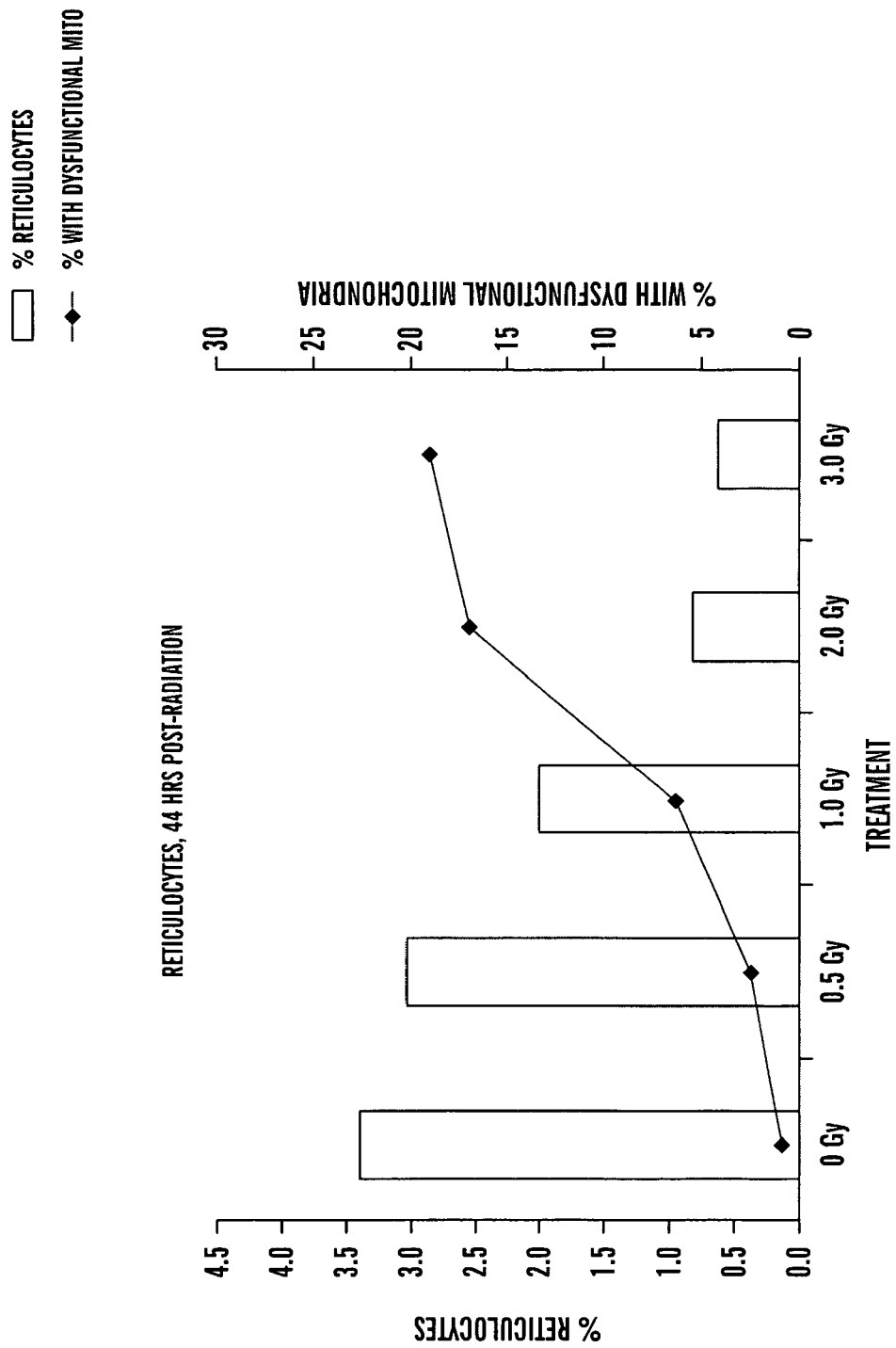

Platelet, reticulocyte, and lymphocyte populations were quantitatively scored according to the procedures described by this invention, and average values for each treatment group are graphed (FIGS. 3A-C).

Example 3

Matrix of Radiation Sensitive Endpoints Using Human Blood

This example used human blood, thereby serving to demonstrate the compatibility of the invention with blood of this origin. Furthermore, one fraction of blood was treated ex vivo with carbonyl cyanide 3-chlorophenylhydrazone (CCCP), a toxic chemical that is known to disrupt mitochondrial membrane potential. This example therefore also demonstrates the specificity of the TMRE-associated fluorescence signal.

Blood from a finger prick (approximately 150 μl) was collected into a tube containing 10 μl heparin solution (500 Units/ml; approximately 6% dilution). One 5 μl aliquot of heparinized whole blood was added to a tube with 1 ml Hank's Balance Salt Solution containing SYTO®13 at 5 nM, TMRE at 100 nM, and 20,720 counting beads per ml (beads from Molecular Probes, cat. no. C36950) (i.e., blood diluted another 200-fold). A second fraction of blood was treated with 50 μM CCCP before being stained with SYTO®13 and TMRE as above. After staining for 30 minutes at room temperature, the samples were analyzed with a FACSCalibur flow cytometer providing 488 nm excitation.

Figure 4A:
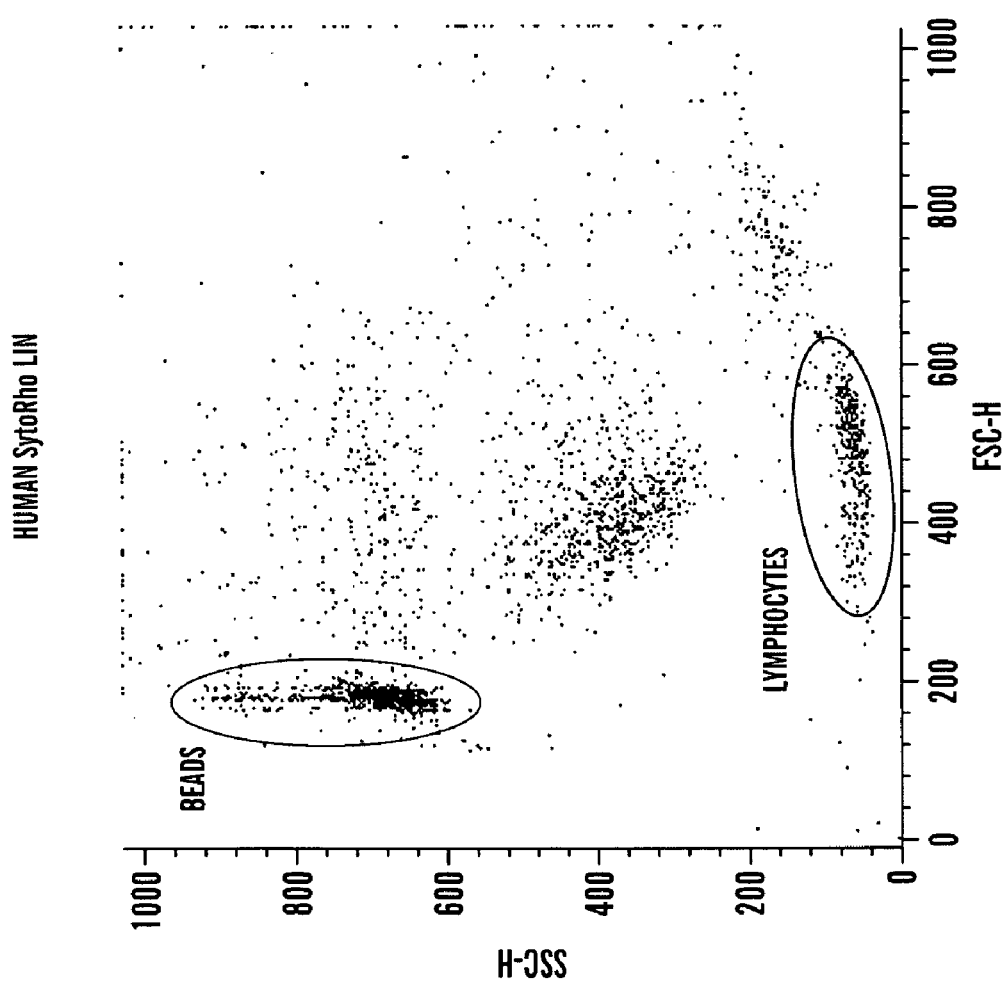
FIGS. 4A-C show bivariate plots from flow cytometric analyses of a human blood specimen. In this example, whole blood was simultaneously contacted with SYTO®13 (a FL1 channel dye) and tetramethylrhodamine ethyl ester (TMRE; a FL2 channel dye), and a known number of microspheres were included as counting beads.

Acquisition was triggered with a FL1 threshold that was set sufficiently high so as to exclude platelets, mature erythrocytes and reticulocytes, thereby restricting acquisition to nucleated cells. By expressing light scatter in linear scale, it was possible to focus on particular subpopulations, for instance lymphocytes that are low in forward and side scatter relative to other nucleated cells (FIG. 4A). Since the counting beads are highly fluorescent, they were not excluded by the FL1 threshold, and their known density facilitated lymphocyte counting that can be expressed on a per volume basis (see Table IV). Furthermore, with the incorporation of the TMRE dye, it was possible to enumerate the percentage of lymphocytes that express dysfunctional mitochondrial membranes.

Figure 4B:
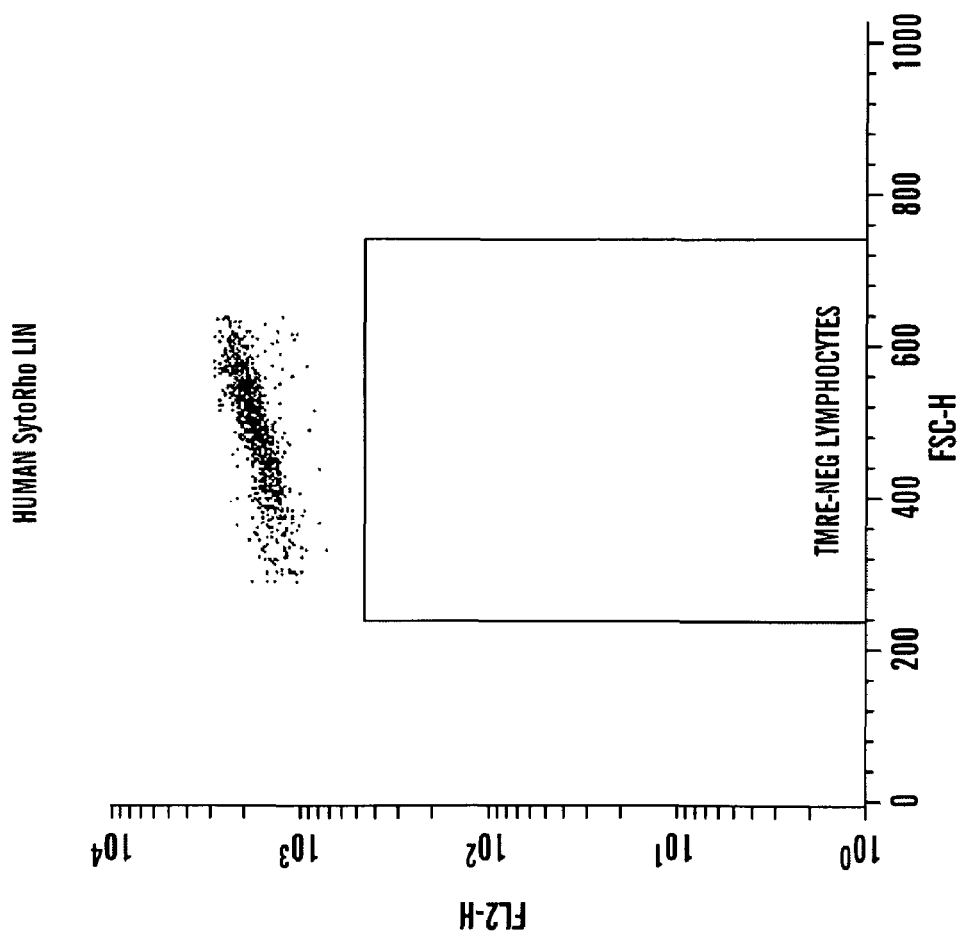
Figure 4C:
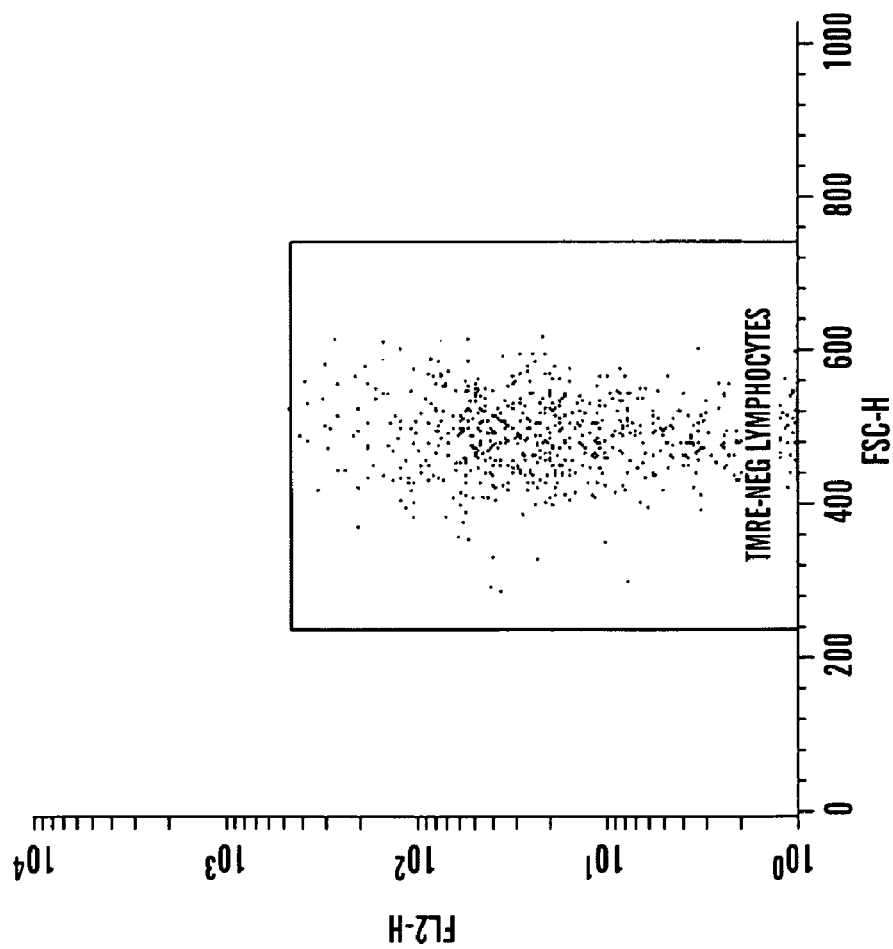

As shown by FIG. 4B, the frequency of lymphocytes that exhibit a TMRE-negative phenotype is very low in this healthy volunteer. On the other hand, when mitochondrial dysfunction has been induced, for instance through ex vivo exposure to CCCP, loss of TMRE-associated signal leads to increased incidence of events falling into this region (FIG. 4C).

TABLE IV

Lymphocyte counts in adult volunteer

| Bead Density (per ml) | FCM: Bead Count | FCM: Lymphocyte Count | FCM: Volume Analyzed | Lymphocytes per L | Lymphocytes per L† |
|---|---|---|---|---|---|
| 20,720 | 3,490 | 1,115 | 0.168 ml | $6.64 \times 10^6$ | $1.41 \times 10^9$ |

†Adjusted for Dilution Factor

Example 4

Radioprotectant Evaluation Using Mouse Blood

This example demonstrates the ability of the invention to assess modifiers of hematotoxicity, in this case, a radioprotectant drug.

In this experiment, one group of five C57BL/6J mice was sham irradiated, whereas two other groups of five mice were exposed to 1 Gy gamma rays. While one group of irradiated mice was injected with vehicle, the other was injected with the radioprotectant agent amifostine (400 mg/kg injected ip, 30 minutes prior to irradiation). Blood was collected 46±3 hrs post-irradiation into a low volume of heparin that did not appreciably dilute the samples.

5 µl of whole blood were added to tubes containing 1 ml HBSS with SYTO®13 at 10 nM, TMRE at 100 nM, and 20,720 counting beads per ml (beads from Molecular Probes, cat. no. C36950). After 30 minutes at room temperature, the samples were moved to 4° C. and analyzed with a FACSCalibur flow cytometer providing 488 nm excitation.

In the first round of analysis, a forward scatter threshold was used to trigger data acquisition. With the trigger channel set sufficiently low, platelets as well as all blood cell types were acquired. Similar to thiazole orange, SYTO®13 dye in conjunction with light scatter signals was capable of resolving mature erythrocytes, reticulocytes, nucleated cells, platelets, and reticulated platelets. As nucleated cells exhibit intense SYTO®13-associated fluorescence, these events can be excluded from measurements that were directed at platelet and erythrocyte populations. Reticulocytes can thus be quantified as a percentage of all erythrocytes, and reticulated platelets can be quantified as a percentage of all platelets. Furthermore, with the incorporation of the TMRE dye, it was possible to enumerate the percentage of reticulocytes that express dysfunctional mitochondrial membranes.

A second analysis was conducted with the stained rat blood specimens. Whereas acquisition had been triggered on forward light scatter and light scatter was acquired in log scale in the first analysis, the second analysis occurred with a FL1 threshold and light scatter was acquired in linear scale. Regarding the FL1 threshold, this was set sufficiently high so as to exclude platelets, mature erythrocytes and reticulocytes, thereby restricting acquisition to nucleated cells. By expressing light scatter in linear scale, it was possible to focus on particular subpopulations, for instance lymphocytes that are low in forward and side scatter relative to other nucleated cells. Since the counting beads are highly fluorescent, they were not excluded by this FL1 threshold, and their known density facilitated lymphocyte counting that can be expressed on a per volume basis. Furthermore, with the incorporation of the TMRE dye, it was possible to enumerate the percentage of lymphocytes that express dysfunctional mitochondrial membranes.

Figure 5A:
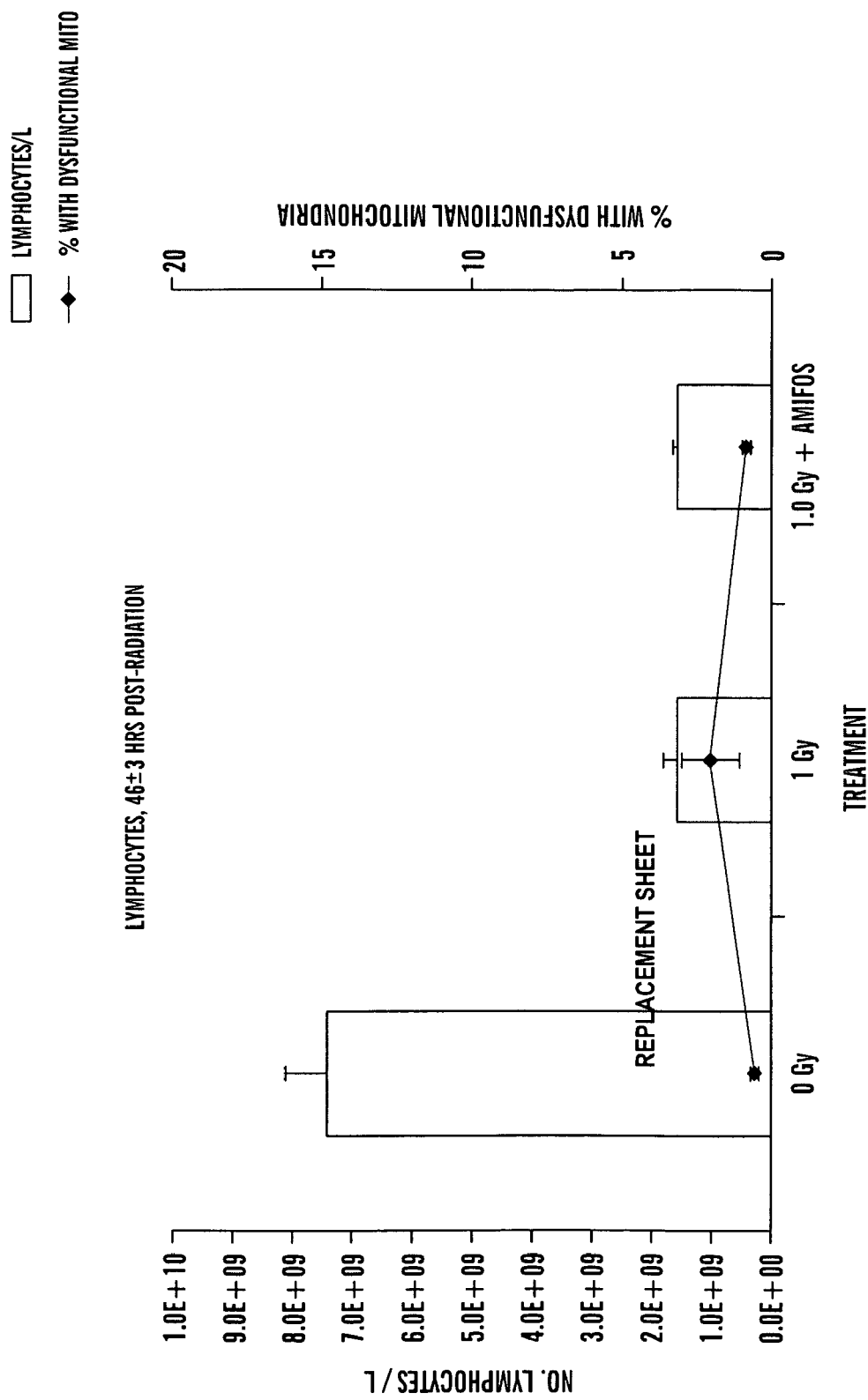
FIGS. 5A-B are graphs showing the effects that in vivo exposure to gamma rays has on four endpoints measured in this invention. These data are from groups of five female C57BL/6J mice exposed to 0 or 1 Gy, or else 1 Gy plus the known radioprotectant agent amifostine (400 mg/kg injected ip, 30 minutes prior to irradiation). Blood was collected 46±3 hrs post-irradiation.
Figure 5B:
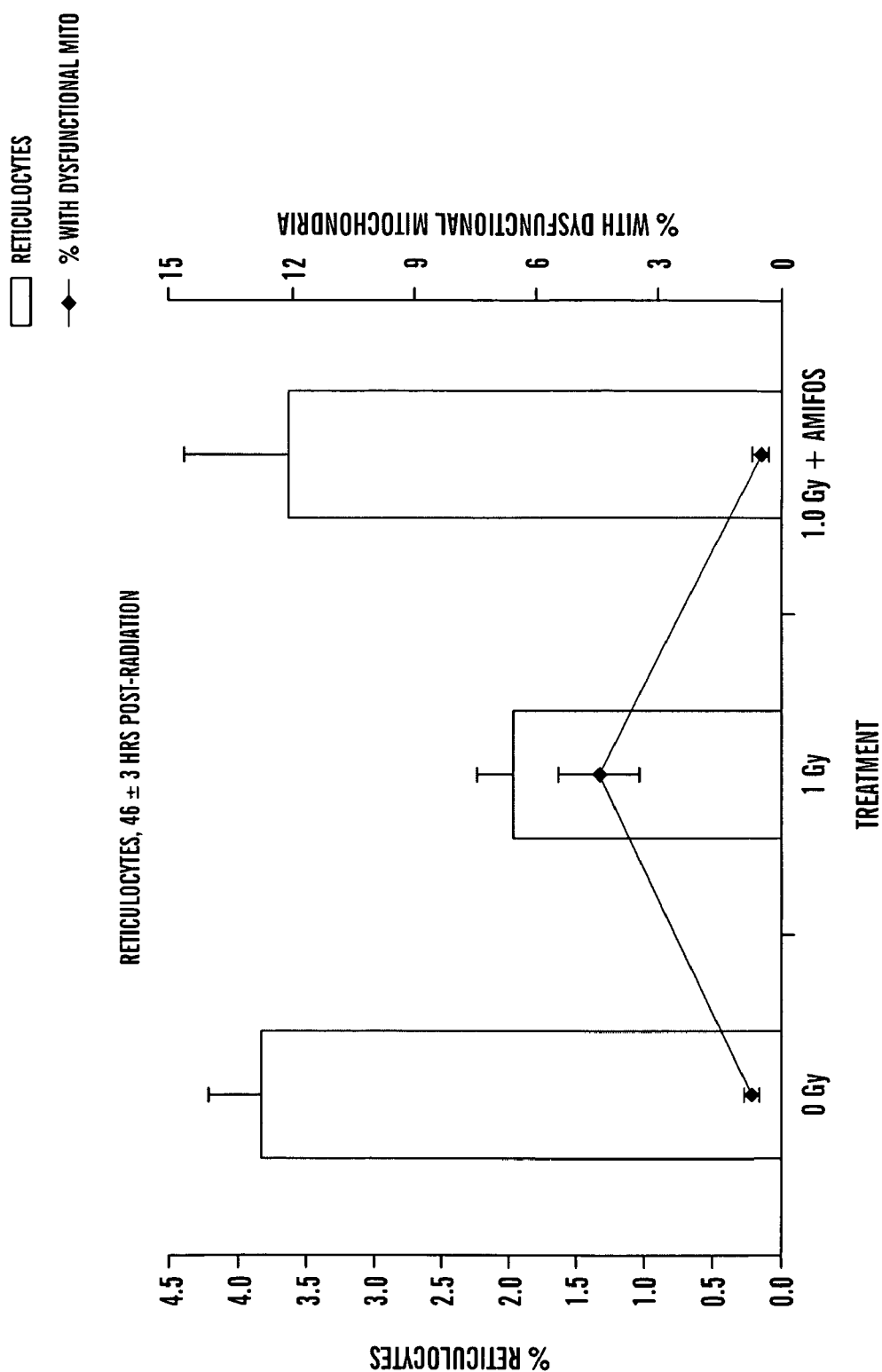

As shown by FIGS. 5A-B, the percentage of lymphocytes is decreased by 1 Gy irradiation, with no appreciable protection afforded by amifostine. Reticulocytes are also found to decrease given 1 Gy treatment, with a marked increase in the percentage of reticulocytes with dysfunctional mitochondria. Unlike lymphocytes, reticulocyte effects are ameliorated by amifostine.

Example 5

Kinetics of Radiation Sensitive Endpoints Using Mouse Blood

This example demonstrates the kinetics by which several radioresponsive endpoints change when mice are exposed to total body gamma rays.

Blood specimens (8-9 week old C57B1/6J) were collected via submandibular puncture from female mice that were exposed to 1, 3 or 6 Gy gamma rays ($^{137}$Cs source). The same 15 animals (5 per treatment group) were bled three times in order to obtain 1, 3 and 6 hr blood specimens. Ten additional animals were exposed to 1, 3 and 6 Gy, half of which were used for a 24 hr blood draw, with the remaining providing the 48 hr blood specimens. This experimental design was used to conserve animals, and also to reduce the effect that repeat bleeding may have on our measurements, especially reticulocyte frequencies, since even low volume blood draws can stimulate erythropoiesis in mice.

Upon submandibular puncture, approximately 20 µl of whole blood was drawn into heparin-coated capillary tubes. These blood volumes were transferred to small tubes and placed on ice until 5 µl were added to tubes containing 1 ml Hank's Balanced Salt Solution with SYTO®13 at 10 nM, TMRE at 100 nM, and 20,720 counting beads per ml (beads from Molecular Probes, cat. no. C36950). After 30 minutes at room temperature, the samples were moved to 4° C. and analyzed with a FACSCalibur flow cytometer providing 488 nm excitation.

In the first round of analysis, a forward scatter threshold was used to trigger data acquisition. With the trigger channel set sufficiently low, platelets as well as all blood cell types were acquired. SYTO®13 dye in conjunction with light scatter signals was capable of resolving mature erythrocytes, reticulocytes, nucleated cells, platelets, and reticulated platelets. As nucleated cells exhibit intense SYTO®13-associated fluorescence, these events can be excluded from measurements that were directed at platelet and erythrocyte populations. Reticulocytes can thus be quantified as a percentage of all erythrocytes, and reticulated platelets can be quantified as a percentage of all platelets. Furthermore, with the incorporation of the TMRE dye, it was possible to enumerate the percentage of reticulocytes that express dysfunctional mitochondrial membranes.

A second analysis was conducted with the stained mouse blood specimens. Whereas acquisition had been triggered on forward light scatter and light scatter was acquired in log scale with the first analysis, the second analysis occurred with a FL1 threshold and light scatter was acquired in linear scale. Regarding the FL1 threshold, this was set sufficiently high so as to exclude platelets, mature erythrocytes and reticulocytes, thereby restricting acquisition to nucleated cells. By expressing light scatter in linear scale, it was possible to focus on particular subpopulations, for instance lymphocytes that are low in forward and side scatter relative to other nucleated cells. Since the counting beads are highly fluorescent, they were not excluded by this FL1 threshold, and their known density facilitated lymphocyte counting that can be expressed on a per volume basis. Furthermore, with the incorporation of the TMRE dye, it was possible to enumerate the percentage of lymphocytes that express dysfunctional mitochondrial membranes.

Figure 6A:
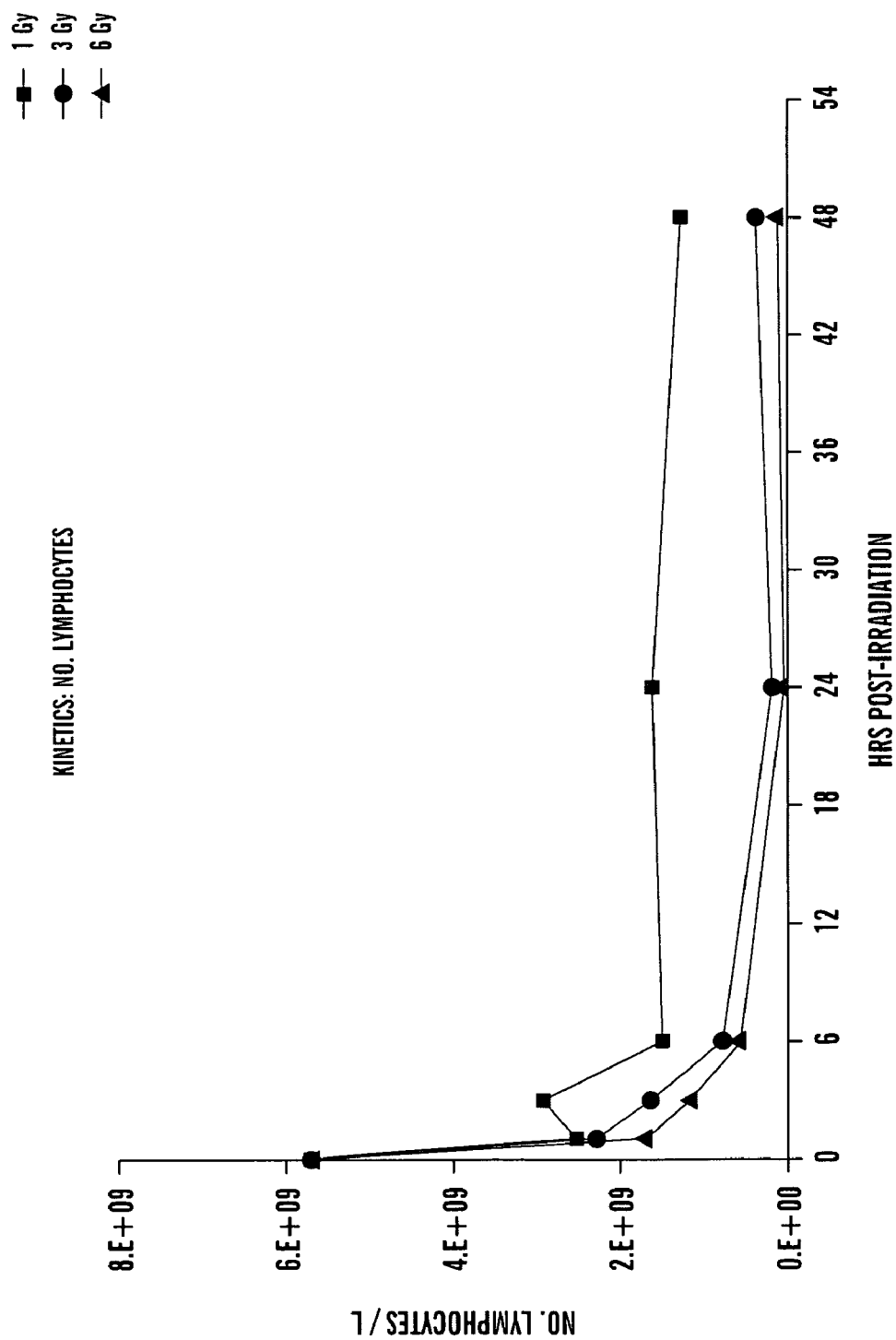
Figure 7A:
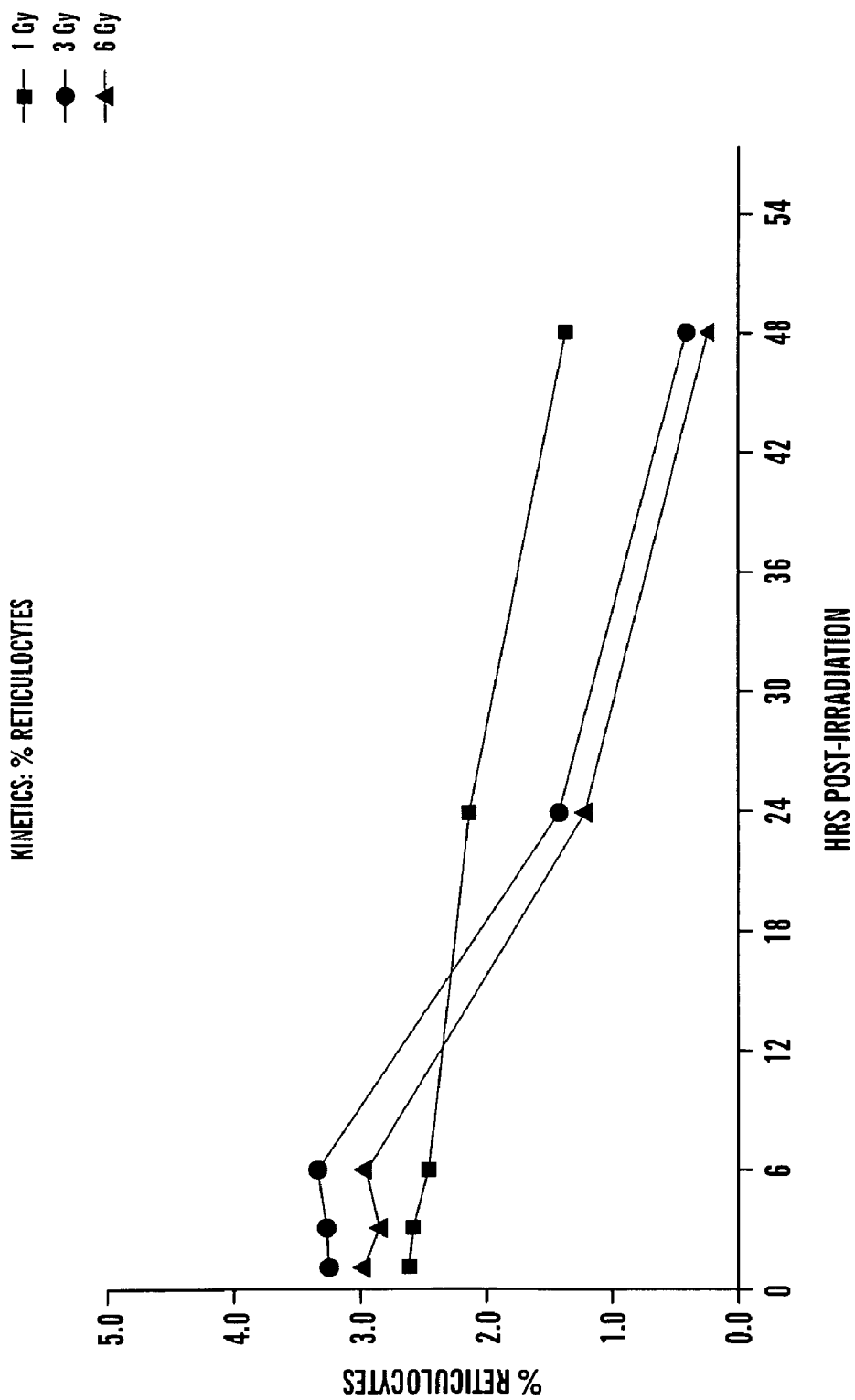
FIGS. 7A-B are graphs showing the effects that in vivo exposure to gamma rays has on two reticulocyte-associated endpoints measured in this invention. These time course data are from groups of female C57BL/6J mice exposed to 1, 3 or else 6 Gy.
Figure 7B:
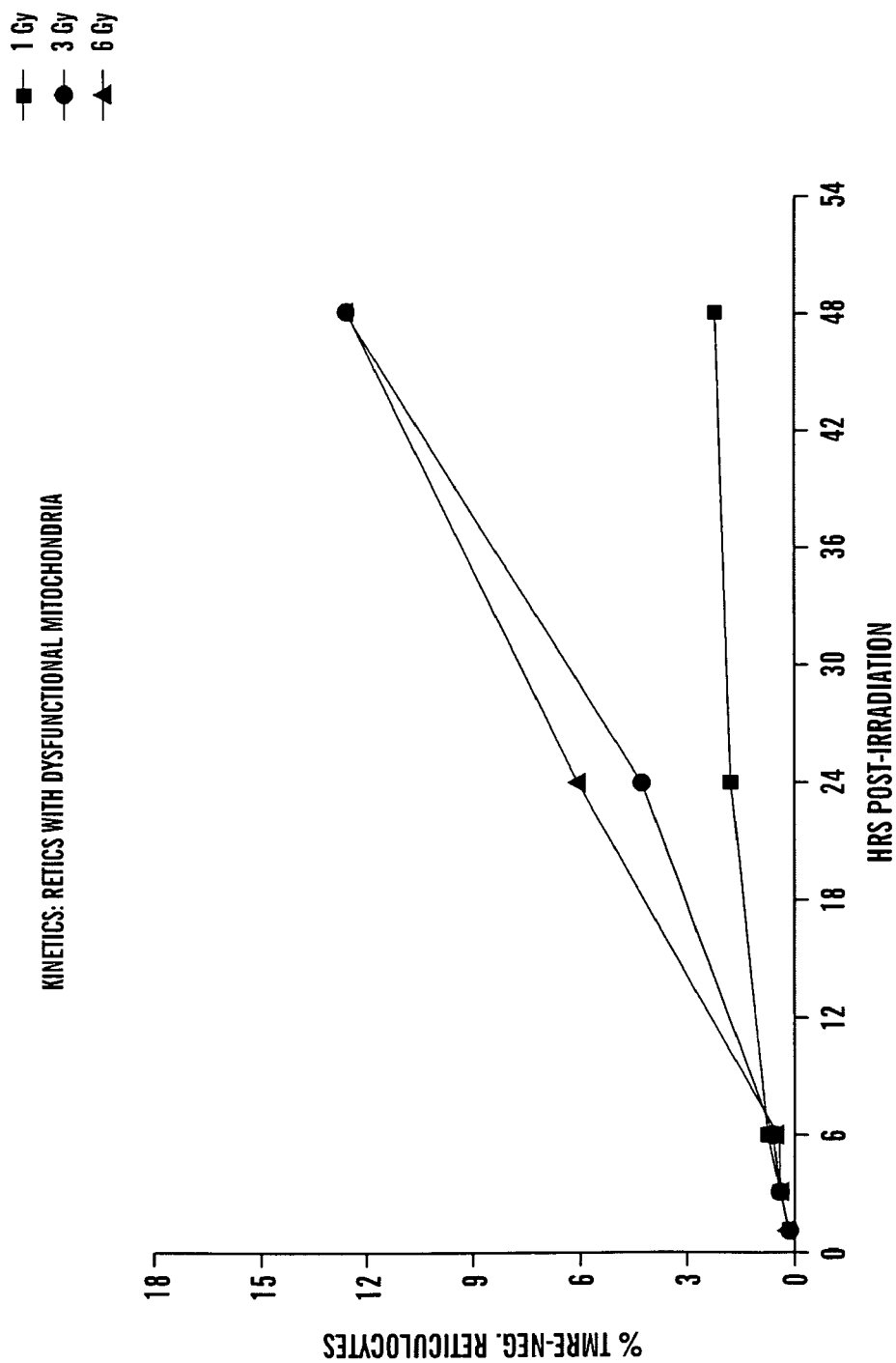

Both reticulocyte and lymphocyte populations were found to be particularly sensitive to the gamma radiation treatment over this 48 hr time frame. Numbers of blood lymphocytes were observed to drop appreciably within hours of treatment, with a concurrent increase in the frequency of TRME-negative lymphocytes (FIGS. 6A-B). On the other hand, blood reticulocytes and the percentage of TRME-negative reticulocytes were stable for at least 6 hrs post-treatment. At the later time points, the frequency of reticulocytes and TRME-negative reticulocytes were observed to either fall or rise sharply, respectively (FIGS. 7A-7B).

Example 6

Matrix of Radiation Sensitive Endpoints Using Rat Blood

This example demonstrates the sensitivity of several endpoints to ionizing radiation in a rat model. For this experiment, SYTO®13 was used to differentially stain blood erythrocytes, reticulocytes, and nucleated cells. TMRE was used to as a mitochondrial membrane probe, and fluorescent latex beads were used as counting beads.

Blood from female Sprague Dawley rats (16 weeks old) was collected via heart puncture following exposure to 0 or 2 Gy gamma rays ($^{137}$Cs source). These specimens were collected approximately 48 hours post-exposure into a low volume of heparin that did not appreciably dilute the samples.

5 μl of whole blood were then added to tubes containing 1 ml HBSS with SYTO®13 at 10 nM, TMRE at 100 nM, and 20,720 counting beads per ml (beads from Molecular Probes, cat. no. C36950). After 30 minutes at room temperature, the samples were moved to 4° C. and analyzed with a FACSCalibur flow cytometer providing 488 nm excitation.

In the first round of analysis, a forward scatter threshold was used to trigger data acquisition. With the trigger channel set sufficiently low, platelets as well as all blood cell types were acquired. SYTO®13 dye in conjunction with light scatter signals was capable of resolving mature erythrocytes, reticulocytes, nucleated cells, platelets, and reticulated platelets. As nucleated cells exhibit intense SYTO®13-associated fluorescence, these events can be excluded from measurements that were directed at platelet and erythrocyte populations. Reticulocytes can thus be quantified as a percentage of all erythrocytes, and reticulated platelets can be quantified as a percentage of all platelets. Furthermore, with the incorporation of the TMRE dye, it was possible to enumerate the percentage of reticulocytes that express dysfunctional mitochondrial membranes.

A second analysis was conducted with the stained rat blood specimens. Whereas acquisition had been triggered on forward light scatter and light scatter was acquired in log scale with the first analysis, the second analysis occurred with a FL1 threshold and light scatter was acquired in linear scale. Regarding the FL1 threshold, this was set sufficiently high so as to exclude platelets, mature erythrocytes and reticulocytes, thereby restricting acquisition to nucleated cells. By expressing light scatter in linear scale, it was possible to focus on particular subpopulations, for instance lymphocytes that are low in forward and side scatter relative to other nucleated cells. Since the counting beads are highly fluorescent, they were not excluded by this FL1 threshold, and their known density facilitated lymphocyte counting that can be expressed on a per volume basis. Furthermore, with the incorporation of the TMRE dye, it was possible to enumerate the percentage of lymphocytes that express dysfunctional mitochondrial membranes.

Figure 8A:
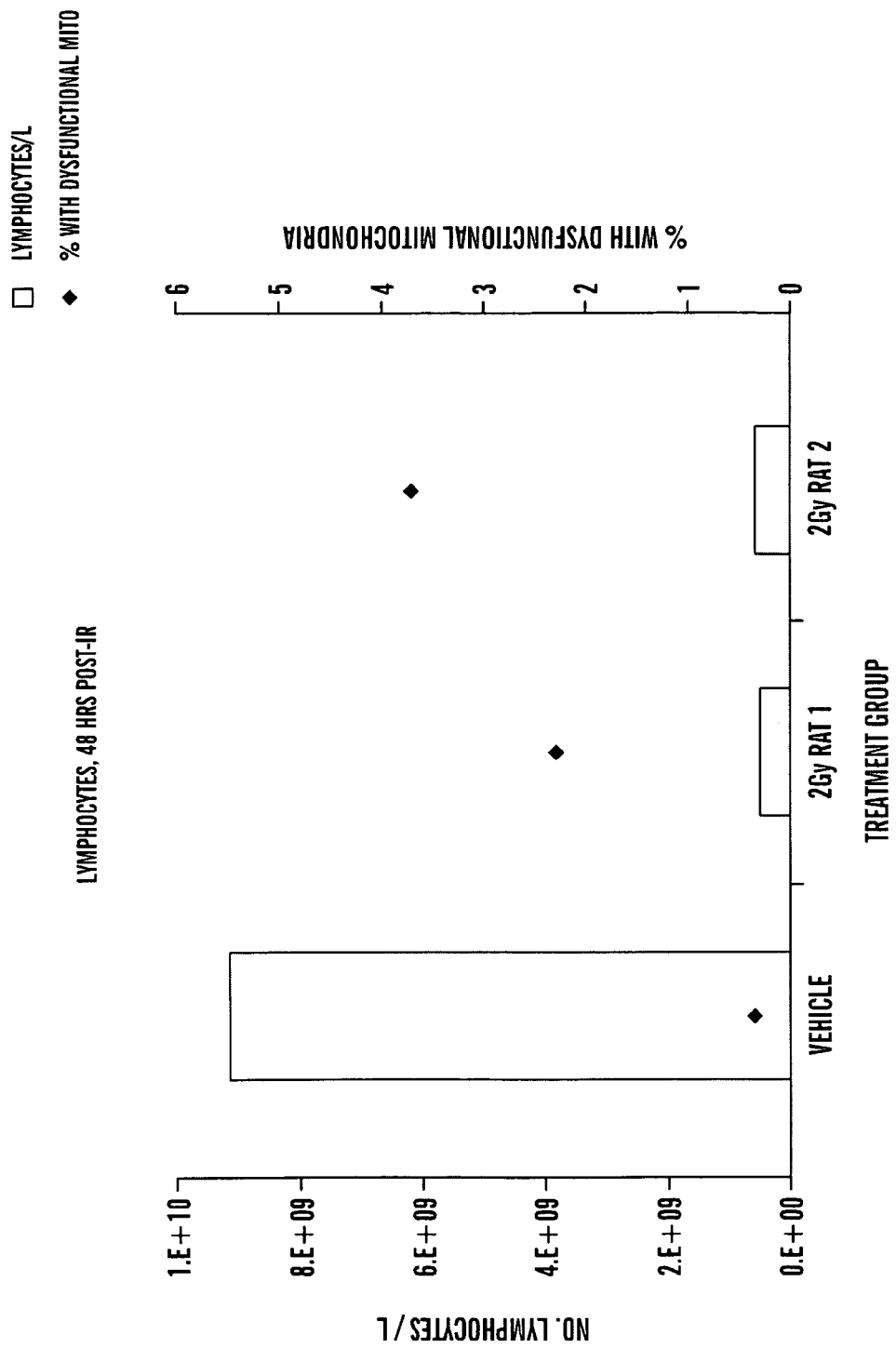
FIGS. 8A-B are graphs showing the effects that in vivo exposure to gamma rays has on four endpoints measured in this invention. These data are from three Sprague Dawley rats exposed to either 0 or 2 Gy, with blood collected 48 hrs post-exposure.
Figure 8B:
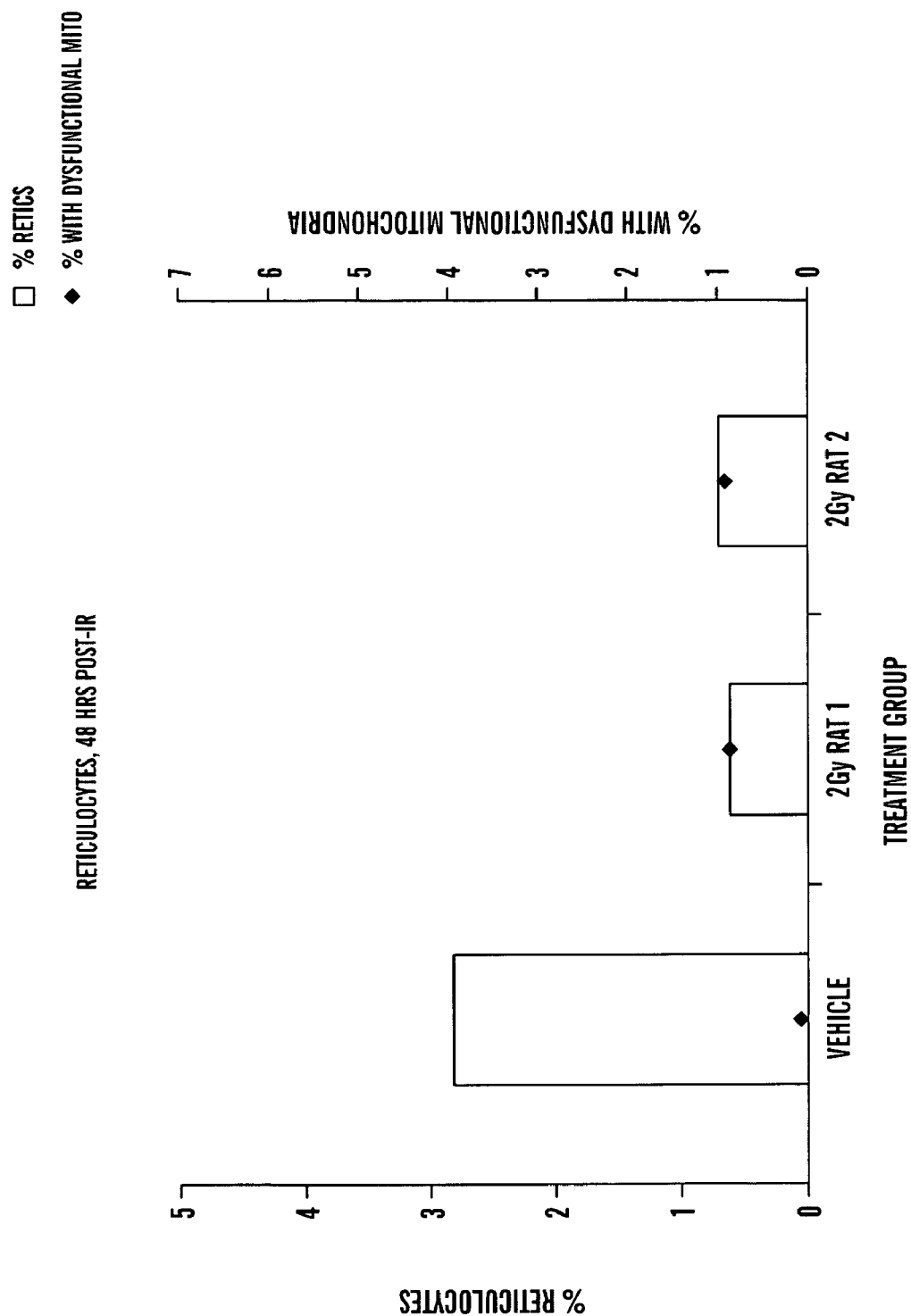

Lymphocyte and reticulocyte data that were collected are shown by FIGS. 8A-B, respectively. As expected from the results shown in FIGS. 3A-C, radiation exposure reduced the lymphocyte and reticulocyte counts and increased mitochondrial damage.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for enumeration of blood cells and blood platelets to assess the degree of hematotoxicity resulting from exposure to a hazardous exogenous agent, the method comprising:

providing a blood sample from a mammal exposed to a hazardous exogenous agent, the blood sample comprising erythrocytes, reticulocytes, nucleated cells, and platelets;

first contacting a portion of the sample of known volume with a nucleic acid dye that has a fluorescent emission spectrum and differentially labels mature erythrocytes, reticulocytes, nucleated cells, platelets, and leukocytes based on their nucleic acid content;

second contacting the portion of the sample with a second fluorescent reagent that is responsive to mitochondrial membrane potential and thereby differentially labels healthy and damaged cells, the second fluorescent reagent having a fluorescent emission spectrum that does not substantially overlap with the fluorescent emission spectrum of the nucleic acid dye;

exciting the nucleic acid dye and second fluorescent reagent with light of appropriate excitation wavelength; and detecting the fluorescent emission and light scatter produced by erythrocytes, reticulocytes, platelets and nucleated cells in the portion of the sample, and counting both (i) the frequency of one or more cell types with and without dysfunctional mitochondria, the cell type being selected from the group consisting of reticulocytes, platelets, reticulated platelets, and leukocytes; and (ii) the absolute number of one or more cell types selected from the group consisting of reticulocytes, platelets, and leukocytes, wherein the counting assesses the degree of hematotoxicity resulting from exposure to the hazardous exogenous agent.

2. The method according to claim 1, wherein the leukocytes comprise lymphocytes and neutrophils.

3. The method according to claim 1 wherein the nucleic acid dye is a cell-permeant cyanine nucleic acid stain or acridine orange.

4. The method according to claim 1 wherein the second fluorescent reagent is tetramethylrhodamine ethyl ester (TMRE); tetramethylrhodamine methyl ester (TMRM); 3,3' dihexyloxacarbocyanine iodide (DiOC$_6$); 5,5',6,6'-tetrachloro-1,1',3,3'-tetraethylbenzimidazolcarbocyanine iodide (JC-1); 3,3-dimethyl-α-naphthoxacarbocyanine iodide (JC-9); 1,1',3,3',3'-hexamethylindodicarbocyanine iodide (DilC$_1$); nonylacridine orange; safranine O; or rhodamine-123.

5. The method according to claim 1 wherein said first contacting and said second contacting are carried out simultaneously.

6. The method according to claim 1 wherein said first contacting and said second contacting are carried out sequentially.

7. The method according to claim 1 further comprising:
introducing a known volume of a known concentration of fluorescent microspheres into the portion of the sample, the fluorescent microspheres having a fluorescent emission spectrum that does not substantially overlap with the fluorescent emission spectra of the nucleic acid dye or the second fluorescent reagent, and
calculating the absolute number of lymphocytes, the absolute number of platelets, and/or the absolute number of neutrophils per unit volume of blood based on the volume of the sample portion and the number of fluorescent microspheres counted.

8. The method according to claim 7 wherein said first contacting, said second contacting, and said introducing are carried out simultaneously.

9. The method according to claim 1 wherein said exciting is carried out with a single-laser or multiple-laser, flow cytometer.

10. The method according to claim 1 wherein said detecting is carried out twice under separate conditions:
(i) at a forward light scatter threshold value set during a first detecting step to include platelets, mature erythrocytes, immature erythrocytes, and nucleated cells; and
(ii) at a fluorescence threshold value set during a second detecting step to eliminate platelets, mature erythrocytes, and immature erythrocytes, thereby restricting analyses to nucleated cells.

11. The method according to claim 1 wherein said providing comprises providing two or more blood samples from the mammal, the two or more blood samples being obtained at different time points relative to the exposure to hazardous agent(s), said method further comprising:
repeating said first contacting, second contacting, exciting, and detecting and counting for each of the samples; and
comparing the results obtained from the two or more samples, wherein changes in the frequency of the one or more cell types with and without dysfunctional mitochondria and the absolute number of the one or more cell types are used to indicate the extent of hematotoxicity associated with the exposure.

12. The method according to claim 11 wherein the changes are in respect to magnitude.

13. The method according to claim 11 wherein the changes are in respect to the rate of change.

14. The method according to claim 11 wherein the changes are in respect to magnitude and rate of change.

15. A method of assessing radiation exposure comprising:
performing the method according to claim 1 on a single blood sample;
identifying the amount of time elapsed between the exposure event and the providing of the single blood sample; and
comparing the results obtained from the single blood sample, with expected values for unexposed mammals, for frequency of the one or more cell types with and without dysfunctional mitochondria and the absolute number of the one or more cell types, wherein deviation from the expected values, in consideration of the elapsed time, indicates the dose level of radiation exposure.

16. A method of assessing radiation exposure comprising:
performing the method according to claim 1 on two or more blood samples obtained from the mammal, the two or more blood samples being obtained at different time points relative to the radiation exposure;
identifying the amount of time elapsed between the radiation exposure event and the providing of the two or more blood samples; and
comparing the results obtained from the two or more blood samples for frequency of the one or more cell types with and without dysfunctional mitochondria and the absolute number of the one or more cell types, wherein the rate at which frequency and absolute number values change, the magnitude of frequency and absolute number value change, or the combination thereof, indicates the level of radiation exposure.

17. A method of evaluating the effects of an exogenous agent that can modify hematotoxicity comprising:
administering to a mammal an exogenous agent that may modify hematotoxicity, and a known hematotoxic agent;
performing the method according to claim 1 on a blood sample obtained from the mammal to obtain two or more endpoints; and
comparing the values for the frequency of the one or more cell types with and without dysfunctional mitochondria and the absolute number of the one or more cell types for the mammal with corresponding frequency and absolute number values obtained for unexposed mammals and/or mammals exposed to the known hematotoxic agent, wherein a significant deviation in the frequency and absolute number values indicates the degree to which the exogenous agent can modify hematotoxicity.

\* \* \* \* \*